United States Patent
Huang

(10) Patent No.: US 11,324,750 B2
(45) Date of Patent: May 10, 2022

(54) COMPOSITIONS AND METHODS FOR THE TREATMENT OF SEVERE ACUTE RESPIRATORY SYNDROME CORONAVIRUS 2 (SARS-COV-2) INFECTION

(71) Applicant: Children's Hospital Medical Center, Cincinnati, OH (US)

(72) Inventor: Gang Huang, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 17/131,875

(22) Filed: Dec. 23, 2020

(65) Prior Publication Data

US 2021/0322421 A1 Oct. 21, 2021

Related U.S. Application Data

(60) Provisional application No. 63/007,477, filed on Apr. 9, 2020.

(51) Int. Cl.
*A61K 31/519* (2006.01)
*A61K 31/56* (2006.01)
(Continued)

(52) U.S. Cl.
CPC .......... *A61K 31/519* (2013.01); *A61K 9/0053* (2013.01); *A61P 31/14* (2018.01); *A61K 31/573* (2013.01)

(58) Field of Classification Search
CPC .................................................. A61K 31/519
(Continued)

(56) References Cited

U.S. PATENT DOCUMENTS 7,598,257 B2 10/2009 Rodgers et al.
7,622,559 B2 11/2009 Teeling et al.
(Continued)

FOREIGN PATENT DOCUMENTS

WO WO 2014/205132 A2 1/2014
WO WO 2016/035014 A1 3/2016

OTHER PUBLICATIONS

Novartis ("Ruxolitinib managed access program (MAP) for patients diagnosed with COVID-19and have severe/very severe lung disease" (Mar. 25, 2020), approved on Apr. 2, 2020 (Year: 2020).*
(Continued)

*Primary Examiner* — Shengjun Wang
(74) *Attorney, Agent, or Firm* — Frost Brown Todd LLC; Nicole M. Tepe

(57) ABSTRACT

Disclosed herein are methods for treating an individual having a Severe Acute Respiratory Syndrome Coronavirus 2 (SARS-CoV-2) infection. The method may comprise administering a JAK inhibitor, for example ruxolitinib (JAKAFI®), to an individual in need thereof, such individual generally being an individual having, or suspecting of having, SARS-CoV-2 infection. The individual in need thereof may be an individual having, or suspected of having or at risk for developing SARS-CoV-2 infection-related cytokine storm. The individual in need thereof may further be an individual having, or suspected of having SARS-CoV-2 infection-related pneumonia.

26 Claims, 6 Drawing Sheets

Specification includes a Sequence Listing.

(51) Int. Cl.
  *A61K 31/155* (2006.01)
  *A61P 31/14* (2006.01)
  *A61K 9/00* (2006.01)
  *A61K 31/573* (2006.01)

(58) Field of Classification Search
  USPC .................................................. 514/265.1
  See application file for complete search history.

(56) References Cited

U.S. PATENT DOCUMENTS

| | | | |
|---|---|---|---|
| 8,142,777 | B2 | 3/2012 | Hamilton et al. |
| 8,529,893 | B2 | 9/2013 | Welcher et al. |
| 8,722,693 | B2 | 5/2014 | Rodgers et al. |
| 8,956,607 | B2 | 2/2015 | Osterroth et al. |
| 8,992,920 | B2 | 3/2015 | Smith |
| 10,022,378 | B2 | 7/2018 | Gavegnano et al. |
| 10,703,814 | B2 | 7/2020 | Ellis et al. |
| 11,045,546 | B1 | 6/2021 | Kelly et al. |
| 2018/0252727 | A1 | 9/2018 | Garfall et al. |
| 2019/0269744 | A1 | 9/2019 | Tufaro et al. |
| 2019/0336504 | A1* | 11/2019 | Gill .......................... A61P 37/02 |

OTHER PUBLICATIONS

Italian Medicine Agency Italian Medicine Agency website https://www.aifa.gov.it/en/programmi-di-uso-compassionevole-covid-19, Apr. 3, 2020 (Year: 2020).*

Vannucchi et al. "Compassionate use of JAK1/2 inhibitor ruxolitinib for severe COVID-19: a prospective observation study " Leukemia, published online Aug. 19, 2020 https://www.nature.com/articles/s41375-020-01018-y.pdf (Year: 2020).*

Kenderian et al. "Ruxolitinib prevents cytokine release syndrome after Car T-cell therapy without impairing the anti-tumor effect in a xenograft model," Biol. Blood Marrow Transplant, 2017, vol. 23, pp S19-S20 (Year: 2017).*

Wang et al. "The definition and risks of cytokine release syndrome— like in 11 COVID-19-infected Pneumonia critically ill patients: Disease characteristics and retrospective analysis," medRxiv preprint Feb. 26, 2020. alhttps://www.medrxiv.org/content/10.1101/2020.02.26.20026989v1.full.pdf (Year: 2020).*

Wang et al. "Adjuvant treatment with a mammalian target of rapamycin inhibitor, sirolimus, and steroids improve outcomes in patients with sever H1N1 pneumonia and acute respiratory failure," Critical Care Medicine, 2014, vol. 42, No. 2, pp. 313-321, Wang II hereafter. (Year: 2014).*

Clinical Trial NCT04334044 "treatment of SARS caused by COVID-19 with ruxolitinib", https://clinicaltrials.gov/ct2/show/NCT04334044 First posted Apr. 3, 2020 . (Year: 2020).*

Ahmed, A, et al. "Ruxolitinib in adult patients with secondary haemophagocytic lymphohistiocytosis: an open-label, single-centre, pilot trial," Lancet Haematol, 2019, 6(12): e630-e7, 8 pgs.

Ajayi, S., et al. "Ruxolitinib," In: Martens U. (eds) Small Molecules in Hematology. Recent Results Cancer Res, Springer, Cham., Springer Nature 2018, pp. 119-132, 14 pgs.

Albeituni, S., et al., "Mechanisms of action of ruxolitinib in murine models of hemophagocytic lymphohistiocytosis," Blood, 2019, 134(2): 147-159, 21 pgs.

Andrade, L.P. (ed.), "Coronavirus Edition," Journal of Bioengineering and Technology Applied to Health, SENAI Institute of Innovation in Advanced Health Systems—ISI/SENAI CIMATEC, Mar. 2020, vol. 3, No. 1, 113 pgs. (Filed in two parts. Part 1-66 pgs., Part 2, 47 pgs.).

Applied Stemcell, Inc., Targatt™-HEK293 Master Cell Line & Knock-in Kit, Datasheet, 2020, 9 pgs.

Arnaldez, F.I., et al., "The Society for Immunotherapy of Cancer perspective on regulation of interleukin-6 signaling in COVID-19-related systemic inflammatory response," Journal for ImmunoTherapy of Cancer, 2020, 8:e000930, 12 pgs.

Barosi, G., et al., "Primary myelofibrosis: Older age and high JAK2V617F allele burden are associated with elevated plasma high-sensitivity C-reactive protein levels and a phenotype of progressive disease," Leuk Res, 2017, 60:18-23, 6 pgs.

Blanco-Melo, D., et al. "Imbalanced Host Response to SARS-CoV-2 Drives Development of COVID-19," Cell, 2020, 181:1036-1045, 20 pgs.

Cao, B., et al., "A Trial of Lopinavir-Ritonavir in Adults Hospitalized with Severe Covid-19," N Engl J Med, 2020, 382(19):1787-1799, 13 pgs.

Cao, Y., et al., "Cytokines profiling and their clinical significance analysis of 2019-nCoV pneumonia patients," Tongji Hospital, Tongji Medical College, Hiazhong University of Science and Technology, Wuhan, Hubei, China, Feb. 5, 2020, 3 pgs.

Cao, Y., et al., "Cytokines profiling and their clinical significance analysis of 2019-nCoV pneumonia (novel coronavirus pneumonia, NCP) patients," Tongji Hospital, Tongji Medical College, Hiazhong University of Science and Technology, Wuhan, Hubei, China, Feb. 8, 2020, 3 pgs.

Cao, Y., et al., "Cytokines profiling and their clinical significance analysis of novel coronavirus pneumonia (COVID-19) patients," Tongji Hospital, Tongji Medical College, Hiazhong University of Science and Technology, Wuhan, Hubei, China, Feb. 12, 2020, 3 pgs.

Cao, Y., et al., "Cytokines profiling and their clinical significance analysis of novel coronavirus pneumonia (COVID-19) patients," Tongji Hospital, Tongji Medical College, Hiazhong University of Science and Technology, Wuhan, Hubei, China, Feb. 24, 2020, 3 pgs.

Cao, Y., et al., "Imaging and clinical features of patients with 2019 novel coronavirus SARS-CoV-2: A systematic review and meta-analysis," J Med Virol, 2020, 11 pgs.

Cao, Y., et al., "Ruxolitinib in treatment of severe coronavirus disease 2019 (COVID-19): A multicenter, single-blind, randomized controlled trial," J Allergy Clin Immunol, 2020, 146:137-146, 13 pgs.

Cao, Y., "Severe novel coronavirus pneumonia (COVID-19) patients treated with ruxoliitinib in combination with mesenchymal stem cells: a prospective, single blind, randomized controlled clinical trial," Tongji Hospital, Tongji Medical College, Hiazhong University of Science and Technology, Wuhan, Hubei, China, Mar. 9, 2020, 3 pgs.

Chan, J.F-W., et al., "A familial cluster of pneumonia associated with the 2019 novel coronavirus indicating person-to-person transmission: a study of a family cluster," Lancet, Jan. 24, 2020, 395:513-523, 10 pgs.

Channappanavar, R., et al., "Pathogenic human coronavirus infections: causes and consequences of cytokine storm and immunopathology," Semin Immunopathol, 2017, 39(5): 529-539, 11 pgs.

Chen, H., et al., "Management of cytokine release syndrome related to CAR-T cell therapy," Front Med, 2019, 13(5):610-617, 8 pgs.

Chen, N., et al., "Epidemiological and clinical characteristics of 99 cases of 2019 novel coronavirus pneumonia in Wuhan, China: a descriptive study," Lancet, 2020, 395(10223):507-513, 7 pgs.

Chien, J-Y., et al., "Temporal changes in cytokine/chemokine profiles and pulmonary involvement in severe acute respiratory syndrome," Respirology, 2006, 11(6): 715-722, 8 pgs.

China National Health Commission. Diagnosis and treatment of pneumonitis caused by new coronavirus (trial version 5). Beijing: China National Health Commission, http://www.nhc.gov.cn/yzygj/s7653p/202002/3b09b894ac9b4204a79db5b8912d4440.shtr., Feb. 2020, 3 pgs.

Cooper, A.M., et al., "IL-12p40: an inherently agonistic cytokine," Trends Immunol, 2007, 28(1):33-38, 6 pgs.

Crayne, C.B., et al., "The Immunology of Macrophage Activation Syndrome," Front Immunol, 2019; vol. 10, article: 119, 11 pgs.

Das, R., et al., "Janus kinase inhibition lessens inflammation and ameliorates disease in murine models of hemophagocytic lymphohistiocytosis," Blood, 2016, 127(13):1666-1675, 10 pgs.

Du, Y., et al., "Clinical Features of 85 Fatal Cases of COVID-19 from Wuhan: A Retrospective Observational Study," Am J Respir Crit Care Med, Jun. 1, 2020, 201(11):1372-1379, 8 pgs.

(56) References Cited

OTHER PUBLICATIONS

Gennaro, A.R., (ed.), Remington's Pharmaceutical Sciences, 18$^{th}$ edition, Mack Publishing Company, Easton, Pennsylvania, 1990, 8 pgs. [Table of Contents Only.].
Gennaro, A.R., (ed.) Remington: The Science and Practice of Pharmacy, 19$^{th}$ edition, Mack Publishing Company, Easton, Pennsylvania, 1995, 3 pgs. [Table of Contents Only.].
Gennaro, A.R., (ed.) Remington: The Science and Practice of Pharmacy, 20$^{th}$ edition, Lippincott Williams & Wilkins, 2000, 5 pgs. [Table of Contents Only.].
Greenfield, G., et al., "The ruxolitinib effect: understanding how molecular pathogenesis and epigenetic dysregulation impact therapeutic efficacy in myeloproliferative neoplasms," J Transl Med, 2018. 16(1):360, 16 pgs.
Gu, J., et al., "Multiple organ infection and the pathogenesis of SARS," J Exp Med, 2005, 202(3):415-424, 10 pgs.
Guan, W., et al., "Clinical Characteristics of Coronavirus Disease 2019 in China," N Engl J Med, Feb. 28, 2020, 13 pgs.
Harrison, C., et al., "Ruxolitinib: a potent and selective Janus kinase 1 and 2 inhibitor in patients with myelofibrosis. An update for clinicians," Ther Adv Hematol, 2012, 3(6):341-354, 14 pgs.
Hechinger, A-K., et al., "Therapeutic activity of multiple common γ-chain cytokine inhibition in acute and chronic GVHD," Blood, 2015, 125(3):570-580, 11 pgs.
Huang, C., et al., "Clinical features of patients infected with 2019 novel coronavirus in Wuhan, China," Lancet, 2020, 395(10223):497-506, 10 pgs.
Huang, R., et al., "HIF1A is a critical downstream mediator for hemophagocytic lymphohistiocytosis," Haemotologia, 2017, 102(11):1956-1968, 13 pgs.
Khwaja, A., "KDIGO Clinical Practice Guidelines for Acute Kidney Injury," Nephron Clin Pract, 2012, 120(4):c179-c184, 6 pgs.
Kotch, C., et al., "Tocilizumab for the treatment of chimeric antigen receptor T cell-induced cytokine release syndrome," Expert Rev Clin Immunol, 2019, 15(8): 813-822, 10 pgs.
Kupferschmidt, K., et al., "Race to find COVID-19 treatments accelerates," Science Mar. 27, 2020; 367(6485):1412-1413, 2 pgs.
Lai, C-C., et al., "Asymptomatic carrier state, acute respiratory disease, and pneumonia due to severe acute respiratory syndrome coronavirus 2 (SARS-CoV-2): Facts and myths," J Microbiol Immunol Infect, 2020, 53:404-412, 9 pgs.
Lee, D.W., et al., "Current concepts in the diagnosis and management of cytokine release syndrome," Blood, 2014, 124(2):188-195, Erratum in: Blood. Aug. 20, 2015;126(8):1048, 9 pgs.
Li, Q., et al., "Early Transmission Dynamics in Wuhan, China, of Novel Coronavirus-Infected Pneumonia," N Engl J Med, 2020, 382(13):1199-1207, 9 pgs.
Liang, W., et al., "Development and Validation of a Clinical Risk Score to Predict the Occurrence of Critical Illness in Hospitalized Patients With COVID-19," JAMA Internal Medicine, 2020, 180(8):1081-1089, 9 pgs.
Mahallawi, W.H., et al., "MERS-CoV infection in humans is associated with a pro-inflammatory Th1 and Th17 cytokine profile," Cytokine, 2018, 104:8-13, 6 pgs.
Mahase, E., "Covid-19: WHO declares pandemic because of "alarming levels" of spread, severity, and inaction," BMJ, 2020, 368:m1036, 1 pg.
Meng, G., et al., "Ruxolitinib treatment for SR-aGVHD in patients with EBV-HLH undergoing allo-HSCT," Ann Hematol, 2020, 99(2):343-349, 7 pgs.
Menten, P., et al., "Macrophage inflammatory protein-1," Cytokine Growth Factor Rev, 2002, 13(6):455-481, 27 pgs.
Neelapu, S.S., et al., "Chimeric antigen receptor T-cell therapy—assessment and management of toxicities," Nat Rev Clin Oncol, 2018, 15(1):47-62, 37 pgs.
Novartis, "clinical study of Jakavi® in severe COVID-19 patients and establish international compassionate use program," Press Release, Apr. 2, 2020, 7 pgs.

Olsson, A-K., et al., "VEGF receptor signalling—in control of vascular function," Nat Rev Mol Cell Biol, 2006, 7(5):359-371, 14 pgs.
Ouedraogo, D-D., et al., "COVID-19, chronic inflammatory rheumatic disease and anti-rheumatic treatments," Clinical Rheumatology, 2020, 39:2069-2075, 7 pgs.
Pan, F., et al., "Time Course of Lung Changes on Chest CT During Recovery From Novel Coronavirus (COVID-19) Pneumonia," Radiology, 2020, 295(3):715-721, 15 pgs.
Peiris, J.S.M., et al., "Clinical progression and viral load in a community outbreak of coronavirus-associated SARS pneumonia: a prospective study," Lancet, 2003; 361(9371):1767-1772, 6 pgs.
Przepiorka, D., et al., "FDA Approval Summary: Ruxolitinib for Treatment of Steroid-Refractory Acute Graft-Versus-Host Disease," The Oncologist, 2020, 25:e328-e334, 7 pgs.
Ranieri, V.M., et al., "Acute Respiratory Distress Syndrome: The Berlin Definition," JAMA, 2012, 307(23):2526-2533, 8 pgs.
Rudd, K.E., et al., "Association of the Quick Sequential (Sepsis-Related) Organ Failure Assessment (qSOFA) Score with Excess Hospital Mortality in Adults with Suspected Infection in Low—and Middle-Income Countries," JAMA, 2018, 319(21):2202-2211, 10 pgs.
Schulz, O., et al., "Chemokines and Chemokine Receptors in Lymphoid Tissue Dynamics," Annu Rev Immunol, 2016, 34:203-242, 42 pgs.
Sin, J.H., et al., "Ruxolitinib for secondary hemophagocytic lymphohistiocytosis: First case report," Hematol Oncol Stem Cell Ther, 2019, 12:166-170, 5 pgs.
Stebbing, J., et al., "COVID-19: combining antiviral and anti-inflammatory treatments," Lancet Infect Dis, Apr. 2020, 30:400-402, 3 pgs.
Tefferi, A., et al., "Circulating Interleukin (IL)-8, IL-2R, IL-12, and IL-15 Levels Are Independently Prognostic in Primary Myelofibrosis: A Comprehensive Cytokine Profiling Study," J Clin Oncol, 2011, 29(10): 1356-1363, 8 pgs.
Trantham, T., et al., "Ruxolitinib for the treatment of lymphoma-associated hemophagocytic lymphohistiocytosis: A cautionary tale," J Oncol Pharm Practice, 2020, 26(4):1005-1008, 4 pgs.
Wang, C-H., et al., "Persistence of lung inflammation and lung cytokines with high-resolution CT abnormalities during recovery from SARS," RespirRes, 2005, 6:42, 12 pgs.
Wang, D., et al., "Clinical Characteristics of 138 Hospitalized Patients With 2019 Novel Coronavirus-Infected Pneumonia in Wuhan, China," JAMA, 2020, 323(11): 1061-1069, 9 pgs.
Wang, Y., et al., "Clinical Outcomes in 55 Patients With Severe Acute Respiratory Syndrome Coronavirus 2 Who Were Asymptomatic at Hospital Admission in Shenzhen, China," J Infect Dis, 2020, XX:1-5, 5 pgs.
Wang, J., et al., "Ruxolitinib for refractory/relapsed hemophagocytic lymphohistiocytosis," Haematologica, 2020, 105:e210-e212, 3 pgs.
Wen, X., et al., "Integration of Prealbumin into Child-Pugh Classification Improves Prognosis Predicting Accuracy in HCC Patients Considering Curative Surgery," Journal of Clinical and Translational Hepatology, 2018, 6(4):377-384, 8 pgs.
Wong, C.K., et al., "Plasma inflammatory cytokines and chemokines in severe acute respiratory syndrome," Clin Exp Immunol, 2004, 136(1):95-103, 9 pgs.
World Health Organization, Clinical management of severe acute respiratory infection when novel coronavirus (2019-nCoV) infection is suspected: interim guidance, Jan. 28, 2020. Geneva: World Health Organization; 2020. Ref No.:WHO/nCoV/Clinical/2020.3, 10 pgs.
World Health Organization, Coronavirus disease (COVID-2019) R&D. Geneva: http://www.who.int/blueprint/priority-diseases/key-action/novel-coronavirus/en/, 2020, 10 pgs.
Xu, Z., et al., "Pathological findings of COVID-19 associated with acute respiratory distress syndrome," Lancet Respir Med, 2020, 8:420-422, 3 pgs.
Yan, X., et al., "Evolution characteristics of thoracic lesions of CT of COVID-19 in recovery stage," Radiologic Practice, Apr. 2020, 35(4):428-432, 5 pgs.

(56) References Cited

OTHER PUBLICATIONS

Yao, X., et al., "A pathological report of three COVID-19 cases by minimally invasive autopsies," Clin J Pathol, May 2020, 49(5):411-418, 8 pgs.

Zandvakili, I., et al., "Ruxolitinib as first-line treatment in secondary hemophagocytic lymphohistiocytosis: A second experience," AJH Wiley, 2018, pp. E123-E125, 3 pgs.

Zhang, C., et al., "Cytokine release syndrome in severe COVID-19: interleukin-6 receptor antagonist tocilizumab may be the key to reduce the mortality," Int J Antimicrob Agents, 2020, 55:105954, 6 pgs.

Zhang, L., et al., "D-dimer levels on admission to predict in-hospital mortality in patients with Covid-19," Journal of Thrombosis and Haemostasis: JTH, 2020, 18 pgs.

Zhang, Q., et al., "Clinical trial analysis of 2019-nCoV therapy registered in China," J Med Virol, 2020, 92:540-545, 6 pgs.

Zhang, W., et al., "The use of anti-inflammatory drugs in the treatment of people with severe coronavirus disease 2019 (COVID-19): The Perspectives of clinical immunologists from China," Clinical Immunology, 2020, 214:108393, 5 pgs.

Zhang, Y., et al., "Analysis of Serum Cytokines in Patients with Severe Acute Respiratory Syndrome," Infect Immun, 2004, 72(8):4410-4415, 6 pgs.

Zhonghua, [Chinese guidelines for the diagnosis and treatment of heart failure 2018], Chin J Cardiol, 2018;46(10):760-789, 30 pgs. [Chinese language only.].

Zhou, X., et al., "Recurrent pneumonia in a patient with new coronavirus infection after discharge from hospital for insufficient antibody production: a case report," BMC Infectious Diseases, 2020, 20:500, 4 pgs.

Zhu, N., et al., "A Novel Coronavirus from Patients with Pneumonia in China, 2019," N Engl J Med, 2020, 382(8):727-733, 7 pgs.

Zhu, R., et al., "Systematic Review of the Registered Clinical Trials of Coronavirus Diseases 2019 (COVID-19)" medRxiv, Mar. 2020, 24 pgs.

Bulut, O., et al., "Mesenchymal stem cell derived extracellular vesicles: promising immunomodulators against autoimmune, autoinflammatory disorders and SARS-CoV-2 infection," Turkish Journal of Biology, May 4, 2020, pp. 273-282, 10 pgs.

International Invitation to Pay Additional Fees and, Where Applicable, Protest Fees, dated Mar. 9, 2021 for Application No. PCT/US2020/066621, 2 pgs.

Bassetti, M., et al., "The novel Chinese coronavirus (2019-nCoV) infections: Challenges for fighting the storm," Eur J Clin Invest, 2020, 50:e13209, 4 pgs.

Brudno, J.N., et al., "Toxicities of chimeric antigen receptor T cells: recognition and management," Blood, 2016, 127(26):3321-3330, 10 pgs. https://doi.org/10.1182/blood-2016-04-703751.

Chan, J.K., et al., "Alarmins: awaiting a clinical response," J Clin Invest, 2012, 122(8):2711-2719.

Chen, Z., et al., "T cell responses in patients with COVID-19," Nat Rev Immunol, 2020, 20:529-536, 8 pgs. https://doi.org/10.1038/s41577-020-0402-6.

Chinese Clinical Trial Registry, Index of Versions 1.0-1.7 of Clinical Trial ChiCTR2000029580, 1 pg. http://www.chictr.org.cn/historyversionpuben.aspx?regno=ChiCTR2000029580.

Chinese Clinical Trial, ChiCTR2000029580, Version 1.0, Feb. 8, 2020, 4 pgs. www.chictr.org.cn/hvshowproject.aspx?id=21877.

Egge, K.H., et al., "The anti-inflammatory effect of combined complement and $CD_{14}$ inhibition is preserved during escalating bacterial load," Clin Exp Immunol, 2015, 181:457-467, 11 pgs.

Harrison, C., et al., "JAK Inhibition with Ruxolitinib versus Best Available Therapy for Myelofibrosis," N Engl J Med, 2012, 366:787-798, 29 pgs.

International Search Report and Written Opinion dated May 6, 2021 for Application No. PCT/US2020/066621, 21 pgs.

Gaspari, V., et al., "Side effects of ruxolitinib in patients with SARS-CoV-2 infection: Two case reports," International Journal of Antimicrobial Agents, 2020, 56(2):106023, 2 pg.s.

Gozzetti, A., et al., "The Janus kinase 1/2 inhibitor ruxolitinib in COVID-19," Leukemia, 2020, 34:2815-2816, 2 pgs.

Hasselbalch, H.C., et al., "COVID-19 as a mediator of interferon deficiency and hyperinflammation: Rationale for the use of JAK1/2 inhibitors in combination with interferon," Cytokine and Growth Factor Reviews, 2021, 60:28-45, 18 pgs.

INCYTE, "Incyte Announces Plans to Initiate a Phase 3 Clinical Trial of Ruxolitinib (Jakafi®) as a Treatment for Patients with COVID-19 Associated Cytokine Storm," Business Wire, Incyte Press Release Apr. 2, 2020, downloaded Aug. 10, 2021 from https://www.businesswire.com/news/hone/20200402005731/en/Incyte-Announces-Plans-to-Initiate-a-Phase-3-Clinical-Trial-of-Ruxolitinib-Jakafi-as-a-Treatment-for-Patients-with-COVID-19-Associated-Cytokine-Storm, 4 pgs.

La Rosee, F., et al., "The Janus kinase 1/2 inhibitor ruxolitinib in COVID-19 with severe systemic hyperinflammation," Leukemia, 2020, 34:1805-1815, 11 pgs.

Tisoncik, J.R., et al., "Into the Eye of the Cytokine Storm," Microbiology and Molecular Biology Reviews, 2012, 76(1):16-32, 17 pgs.

European Search Report, Extended, and Written Opinion dated Aug. 18, 2021 for Application No. EP 21167502.0, 9 pgs.

European Search Report, Partial, and Provisional Written Opinion dated Aug. 31, 2021 for Application No. EP 21167513.7, 14 pgs.

Adnkronos, "Coronavirus, first positive outcomes from "anti-intensive care" drug," downloaded from www.adnkronos.com/coronavirus-primi-esiti-positivi-da-farmaco-anti-terapie-intensive_kzSP7ino7VvSyEDTNJ96d, Published Mar. 28, 2020, 3 pgs. (Google translated from Italian).

Bhaskar, S., et al., "Cytokine Storm in COVID-19-Immunopathoiogical Mechanisms, Clinical Considerations, and Therapeutic Approaches: The REPROGRAM Consortium Position Paper," Front Immunol, Hypothesis and Theory, Jul. 10, 2020, 11(Article 1648): 1-16, 16 pgs.

Chen, L., et al., "Elevated serum levels of S100A8/A9 and HMGB1 at hospital admission are correlated with inferior clinical outcomes in COVID-19 patients," Cellular & Molecular Immunology, Jul. 3, 2020, 17:992-994, 3 pgs.

Clinical Trial NCT04331665, "Study of the Efficacy and Safety of Ruxolitinib to Treat COVID-19 Pneumonia," ClinicalTrials.gov, U.S. National Library of Medicine, Apr. 2, 2020, downloaded from https;//clinicaltrials.gov/ct2/show/NCT04331665?term=NCT04331665&draw=2&rank=1, 6 pgs.

Clinical Trial NCT04337359, "Ruxolitinib Managed Access Program (MAP) for Patients Diagnosed With Severe/Very Severe COVID-19 Illness," ClinicalTrials.gov, U.S. National Library of Medicine, Apr. 3, 2020, downloaded from https://clinicaltrials.gov/ct2/show/NCT04337359?term=nct04337359&draw=2&rank=1, 5 pgs.

Clinical Trial NCT04338958, "Ruxolitinib in COVID-19 Patients With Defined Hyperinflammation (RuxCoFlam)," ClinicalTrials.gov, U.S. National Library of Medicine, Apr. 8, 2020, downloaded from https://clinicaltrials.gov/ct2/show/NCT04338958?term=NCT04338958&draw=2&rank=1, 7 pgs.

Clinical Trial NCT04377620, "Assessment of Efficacy and Safety of Ruxolitinib in Participants With COVID-19-Associated ARDS Who Require Mechanical Ventilation (RUXCOVID-DEVENT)," ClinicalTrials.gov, U.S. National Library of Medicine, May 6, 2020, downloaded from https://www.clinicaltrials.gov/ct2/show/NCT04377620, 7 pgs.

Hu, B., et al., "The cytokine storm and COVID-19," J Med Virol, Jun. 27, 2020, 93:250-256, 24 pgs.

INCYTE, "Incyte Announces Results from the Phase 3 DEVENT Study Evaluating Ruxolitinib (Jakafi ®) as a Treatment for Patients with COVID-19 Associated Acute Respiratory Distress Syndrome (ARDS) on Mechanical Ventilation," Incyte.com, Mar. 18, 2021, downloaded from https://investor.incyte.com/press-releases/press-releases/2021/Incyte-Announces-Results-from-the-Phase-3-DEVENT-Study-Evaluating-Ruxolitinib-Jakafi-as-a-Treatment-for-Patients-with-COVID-19-Associated-Acute-Respiratory-Distress-Syndrome-ARDS-on-Mechanical-Ventilation/default.aspx, 6 pgs.

INCYTE, "Incyte COVID-19 Response," Incyte.com, Jun. 11, 2021, downloaded from https://www.incyte.com/COVID-19, 6 pgs.

(56) References Cited

OTHER PUBLICATIONS

Ingraham, N., et al., "Immunomodulation in COVID-19," The Lancet Respiratory Medicine, May 4, 2020, 8:544-546, 3 pgs.

Lucijanic, M., et al., "Ruxolitinib withdrawal due to the COVID-19," Leukemia, 2021, 35:1218, 1 pg.

Malavolta, M., et al., "Exploring the Relevance of Senotherapeutics for the Current SARS-CoV-2 Emergency and Similar Future Global Health Threats," Cells, Apr. 8, 2020, 9:909, 12 pgs.

Novartis, "Novartis provides update on RUXCOVID study of ruxolitinib for hospitalized patients with COVID-19," Novartis.com, Dec. 14, 2020, downloaded from https://www.novartis.com/news/media-releases/novartis-provides-update-ruxcovid-study-ruxolitinib-hospitalized-patients-covid-19?_ga=2.14653567.917090364.1629207225-2081311836.1629207225, 7 pgs.

Shi, H., et al., "Neutrophil calprotectin identifies severe pulmonary disease in COVID-19," medRxiv, Jul. 15, 2020, 20 pgs.

Sohn, K., et al., "COVID-19 patients upregulate toll-like receptor 4-mediated inflammatory signaling that mimics bacterial sepsis," bioRxiv, Jul. 17, 2020, 26 pgs.

Australian Office Action, Examination report No. 1 for standard patent application, dated Jun. 25, 2021 for Application No. AU 2021201783, 10 pgs.

Australian Office Action, Examination report No. 1 for standard patent application, dated Jul. 12, 2021 for Application No. AU 2021201786, 9 pgs.

Chen, L., et al., "Scoring cytokine storm by the levels of MCP-3 and IL-8 accurately distinguished COVID-19 patients with high mortality," Signal Transduction and Targeted Therapy, 2020, 5:292, 3 pgs.

Chen, G., et al., "Clinical and immunological features of severe and moderate coronavirus disease 2019," J Clin Invest, 2020, 130(5):2620-2629, 10 pgs.

Lee, W. J., et al., "Are Prognostic scores and biomarkers such as procalcitonin the appropriate prognostic precursors for elderly patients with sepsis in the emergency department?" Aging Clin Exp Res, 2016, 28:917-924, 8 pgs.

Sun, D., et al., "Clinical features of severe pediatric patients with coronavirus disease 2019 in Wuhan: a single center's observational study," World Journal of Pediatrics, 2020, 16:251-259, 9 pgs.

European Search Report, Extended, and Written Opinion dated Dec. 14, 2021 for Application No. EP 21167513.7, 17 pgs.

* cited by examiner

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Forward Primer MGB Probe

<400> SEQUENCE: 1
tgaccctgtg ggttttacac ttaa                                          24

<210> SEQ ID NO 2
<211> LENGTH: 23
<212> TYPE: DNA
<213> ORGANISM: Artificial Sequence
<220> FEATURE:
<223> OTHER INFORMATION: Reverse Primer MGB Probe

<400> SEQUENCE: 2
cagccataac ctttccacat acc                                           23

<210> SEQ ID NO 3
<211> LENGTH: 19
<212> TYPE: DNA
<213> ORGANISM: Artificial Sequence
<220> FEATURE:
<223> OTHER INFORMATION: FAM Probe 5

<400> SEQUENCE: 3
aacacagtct gtaccgtct                                                19
```

COMPOSITIONS AND METHODS FOR THE TREATMENT OF SEVERE ACUTE RESPIRATORY SYNDROME CORONAVIRUS 2 (SARS-COV-2) INFECTION

CROSS REFERENCE TO RELATED APPLICATIONS

This application claims priority to and benefit of U.S. Provisional Patent Application Ser. No. 63/007,477, filed Apr. 9, 2020, entitled "Compositions and Methods for the Treatment of Severe Acute Respiratory Syndrome Coronavirus 2 (SARS-COV-2) Infection," the contents of which are incorporated by reference in its entirety for all purposes.

BACKGROUND

The end of 2019 witnessed an outbreak of severe acute respiratory syndrome coronavirus 2 (SARS-CoV-2) infection and its associated coronavirus disease 2019 (COVID-19) in Wuhan, China[1,2]. As of Apr. 7, 2020, 1,345,054 total cases and 74,566 deaths in 211 countries & territories with cases have been confirmed. Its rapid global spread has been classified as a pandemic by the World Health Organization[3] and has now represented the most serious issue to public health globally. COVID-19 consists of a heterogeneous disease population, such as asymptomatic carriers, individuals with a mild, self-limiting illness, and patients with severe, or even fatal pneumonia[4]. According to the available clinical information at the time of filing, 80~85% patients with COVID-19 are asymptomatic or mild[5-7], 15-20% patients are severe/critical, of which severe/critical COVID-19 usually induced a high rate of complication and mortality and is a major challenge to clinicians and health care system in most of affected countries[8-10]. In a retrospective study that enrolled 99 cases of COVID-19, 17% patients received mechanical ventilation for 3~22 days and 11% patients eventually died[10]. In a separate study, among 138 hospitalized patients with COVID-19 pneumonia, 26.1% patients were transferred to the intensive care unit (ICU) because of deteriorated complications including 61.1% of them have acute respiratory distress syndrome (ARDS)[8]. Once the patients presented ARDS, most of them responded poorly to current available treatments with an extremely dismal prognosis[9,11]. At the time of filing, no vaccine or specific antiviral agents for SARS-CoV-2 infection was available[12, 13] and supportive therapies played a fundamental role in treatment of COVID-19. While vaccines are on the horizon, there remains a need for improved COVID-19 therapy, in particular, the application of existing clinical drugs in treating severe/critical COVID-19 to improve the poor clinical outcome. The instant disclosure addresses one or more of the aforementioned needs in the art.

BRIEF SUMMARY

Disclosed herein are methods for treating an individual having a Severe Acute Respiratory Syndrome Coronavirus 2 (SARS-CoV-2) infection. In particular, the methods relate to administering a JAK inhibitor, more particularly ruxolitinib (JAKAFI®), to an individual in need thereof, such individual generally being an individual having, or suspecting of having, a SARS-CoV-2 infection (COVID-19). In certain aspects, the individual may be one having, suspected of having, or at risk for developing SARS-CoV-2 infection-related cytokine storm, or may further be an individual having, or suspected of having SARS-CoV-2 infection-related pneumonia.

DETAILED DESCRIPTION

Definitions

Figure 1:
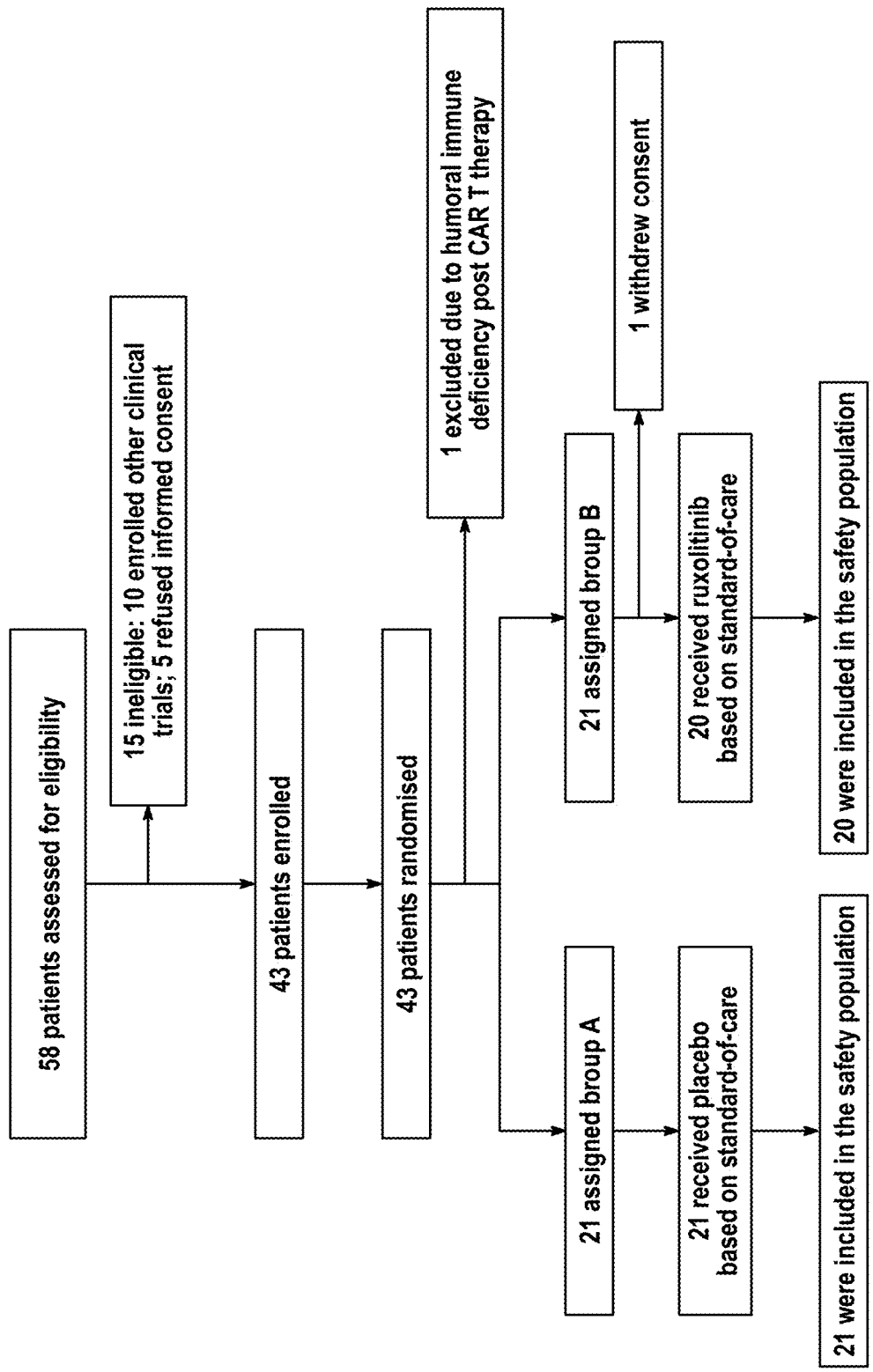
FIG. 1. Randomization and Trial profile.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The active agent may form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps, which may be employed during preparation. Salts of the compounds of the active agent may be formed, for example, by reacting a compound of the active agent with an amount of acid or base, such as an equivalent amount, in a medium such as one in which the salt precipitates or in an aqueous medium followed by lyophilization. When the compounds are in the forms of salts, they may comprise pharmaceutically acceptable salts. Such salts may include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

As of this writing, no therapeutics have yet been proven effective for the treatment of severe COVID-19 with cytokine storm. Ruxolitinib, a potent and selective oral inhibitor of Janus kinase (JAK) 1 and JAK2, was proposed by Applicant to be beneficial in the treatment of cytokine storm. Applicant conducted a prospective, multicenter, single-blind, randomized controlled trial involving participants diagnosed as severe COVID-19 patients, and found that ruxolitinib plus standard of care proved to be a safe and superior treatment of severe COVID-19.

Because Severe Acute Respiratory Syndrome Coronavirus 2 (SARS-CoV-2) infection is a virus infection mediated disease, one of ordinary skill in the art would logically be concerned that the strong inhibition of JAK kinase might inhibit the virus clearance, and as such, would not be useful in treating SARS-CoV-2. Initial research has focused on IL-1, IL-6 and TNF-a to target these specific cytokines individually, despite no understanding of which cytokine is critical to disease progression. Applicant hypothesized that most of the patients exhibiting severe disease had an immune response to clear the virus, and developed cytokine storm that overwhelmed the patient. Applicant has discovered that, despite a belief that strong inhibition of JAK kinase might inhibit clearance of virus, a JAK inhibitor, more particularly ruxolitinib, can in fact be used in in severe patients to treat cytokine storm and allow clearance of the virus and subsequent survival.

Disclosed herein are methods for treating an individual having a Severe Acute Respiratory Syndrome Coronavirus 2 (SARS-CoV-2) infection. The method may comprise administering Ruxolitinib (INCB018424 phosphate, INC424, ruxolitinib phosphate, JAKRFI®) to an individual in need thereof, generally an individual having, or suspecting of having, SARS-CoV-2 infection. Further, the individual in need thereof may be an individual having, or suspected of having or developing SARS-CoV-2 infection related cytokine storm. The individual in need thereof may be an individual having, or suspected of having SARS-CoV-2 infection-related pneumonia, or an individual diagnosed with severe COVID-19 infection. In one aspect, the individual may be one diagnosed with COVID-19 infection and having a B cell deficiency. In a further aspect, the individual may be an individual having one or more of cardiovascular disease (CVD), rheumatoid arthritis (RA), hepatitis, and diabetes.

In one aspect, the immunomodulation therapy may be a JAK kinase inhibitor. In one aspect, the immunomodulation therapy may be an inhibitor of Janus kinase (e.g, JAK1/2). Nonlimiting JAK inhibitors may be selected from Ruxolitinib (Incyte), Baricitinib (Incyte), Tofacitinib (Pfizer), INREBIC (Fedratinib) (Celgene/BMS), and combinations thereof. In one aspect, the JAK inhibitor may be ruxolitinib. Ruxolitinib ((3R)-3-cyclopentyl-3-[4-(7H-pyrrolo[2,3-d]pyrimidin-4-yl)pyrazol-1-yl]propanenitrile) is the first FDA approved Janus kinase (JAK) inhibitor and is the only drug currently approved for treatment of myelofibrosis. Ruxolitinib and the synthesis of ruxolitinib are well known in the art, and described in, for example, U.S. Pat. No. 7,598,257 (which describes a process for the preparation of ruxolitinib), WO2016035014A1 (which relates to processes for the preparation of ruxolitinib and ruxolitinib phosphate), and U.S. Pat. No. 8,722,693 (which relates to sustained-release formulations and dosage forms of ruxolitinib, or a pharmaceutically acceptable salt thereof.) The disclosed methods may use any of the ruxolitinib forms or formulations as described in the aforementioned references, and are not limited to such forms or formulations.

Dosage of the JAK inhibitor may vary. In one aspect, the JAK inhibitor is ruxolitinib and may be administered to an individual at a dose of about 10 mg/day, or about 15 mg/day, or about 20 mg/day, or about 25 mg/day, or about 30 mg/day, or about 35 mg/day, or about 40 mg/day, or about 45 mg/day, or about 50 mg/day, or about 55 mg/day, or about 60 mg/day, or about 65 mg/day, or about 70 mg/day, or about 75 mg/day, or about 80 mg/day, or about 85 mg/day, or about 90 mg/day, or from about 10 to about 100 mg/day, or about 25 to about 75 mg per day, or about 30 to 50 mg/day, or from about 100 to about 200 mg/day, or greater than 200 mg/day. The administration may be carried out once a day, twice a day, three times a day, more than four times a day, or continuously administered throughout a day.

The disclosed methods may further employ the administration of a TYK2 inhibitor. An exemplary TYK2 inhibitor includes BMS-986165, available from Celgene/BMS. In yet another aspect, the methods may further employ the administration of a one or both of a corticosteroid and an anti-viral. In a further aspect, the methods may be carried out in the absence of a steroid.

In a further aspect, the disclosed methods may further employ the administration of one or both of an mTOR inhibition (such as rapamycin) and metformin to said individual, before, during, or after administration of said JAK inhibitor. Sirolimus, also known as rapamycin, is a macrolide compound known in the art used to prevent organ transplant rejection and treat a rare lung disease called lymphangioleiomyomatosis. Rapamycin (sirolimus) is believed to have immunosuppressant functions in humans and is useful in preventing the rejection of kidney transplants. Rapamycin is believed to inhibit activation of T cells and B cells by reducing their sensitivity to interleukin-2 (IL-2) through mTOR inhibition. Metformin, marketed under the trade name Glucophage among others, is the first-line medication for the treatment of type 2 diabetes. In a yet further aspect, the method may further comprise administration of an antiviral antibody, and anti-serum, or anti-viral therapy, in combination with any of the aforementioned active agents, or combination thereof. Such administration of compounds may be in succession or at the same time.

The cytokine storm in COVID-19 is believed to be triggered by macrophage activation and release cytokines. It is associated with lysosome activation, phagocytosis. Metformin and rapamycin are known inhibitors for AMPK and mTOR, which inhibit lysosome activation, and may be used in conjunction with the JAK inhibitors disclosed herein. Chloroquinine/Hydrochloroquinine (CQ/HCQ) function at similar steps with much lower activity. Applicant hypothesizes that Metformin and Rapamycin are likely to work better than CQ/HCQ, and may be used in conjunction with the JAK inhibitors disclosed herein. Cytokine storm in COVID-19 patients is believed to be triggered by macrophage activation and cause release of cytokines, which is associated with lysosome activation, and phagocytosis. Without intending to be limited by theory, it is believed that kinase inhibitors such as ruxolitinib, metformin, and rapamycin are much more potent and specific than chloroquinine/hydroxychloroquinine. Because SARS-CoV-2 infection and disease progress very quickly, there is a need for quickly administering effective treatment for severe patients. Thus, in one aspect, administration according to the aforementioned methods may be implemented immediately following a determination that SARS-CoV-2 infection is severe. In other aspects, the administration may occur immediately upon confirmation or suspicion of SARS-CoV-2 infection, particularly in high risk individuals. It is believed that macrophage activation may be further controlled through inhibiting AMPK/mTOR pathway (using, for example, metformin/rapamycin). This can be administered before, during or after administration of ruxolitinib. In one aspect, the ruxolitinib may be administered following AMPK/mTOR administration.

Pharmaceutical Compositions

In one aspect, active agents provided herein may be administered in a dosage form selected from intravenous or subcutaneous unit dosage form, oral, parenteral, intravenous, and subcutaneous. In some embodiments, active agents provided herein may be formulated into liquid preparations for, e.g., oral administration. Suitable forms include suspensions, syrups, elixirs, and the like. In some embodiments, unit dosage forms for oral administration include tablets and capsules. Unit dosage forms may be configured for administration once a day, twice a day, or more than twice a day.

In one aspect, pharmaceutical compositions are isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions may be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount may be used that will achieve the selected viscosity. Viscous compositions are normally prepared from solutions by the addition of such thickening agents.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents may be advantageously used to maintain good shelf life of the formulation.

When administered orally in liquid form, a liquid carrier such as water, petroleum, oils of animal or plant origin such as peanut oil, mineral oil, soybean oil, or sesame oil, or synthetic oils may be added to the active ingredient(s). Physiological saline solution, dextrose, or other saccharide solution, or glycols such as ethylene glycol, propylene glycol, or polyethylene glycol are also suitable liquid carriers. In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus chosen according to the intended application, such that the characteristics of the carrier are tailored to the selected route of administration. The pharmaceutical compositions may also be in the form of oil-in-water emulsions. The oily phase may be a vegetable oil, such as olive or *arachis* oil, a mineral oil such as liquid paraffin, or a mixture thereof. Suitable emulsifying agents include naturally-occurring gums such as gum acacia and gum tragamayth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

For oral administration, the pharmaceutical compositions may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Aqueous suspensions may contain the active ingredient in admixture with excipients suitable for the manufacture of aqueous suspensions.

Formulations for oral use may also be provided as hard gelatin capsules, wherein the active ingredient(s) are mixed with an inert solid diluent, such as calcium carbonate, calcium phosphate, or kaolin, or as soft gelatin capsules. In soft capsules, the active agents may be dissolved or suspended in suitable liquids, such as water or an oil medium, such as peanut oil, olive oil, fatty oils, liquid paraffin, or liquid polyethylene glycols. Stabilizers and microspheres formulated for oral administration may also be used. Capsules may include push-fit capsules made of gelatin, as well as soft, sealed capsules made of gelatin and a plasticizer, such as glycerol or sorbitol. The push-fit capsules may contain the active ingredient in admixture with fillers such as lactose, binders such as starches, and/or lubricants, such as talc or magnesium stearate and, optionally, stabilizers.

Tablets may be uncoated or coated by known methods to delay disintegration and absorption in the gastrointestinal tract and thereby provide a sustained action over a longer period of time. For example, a time delay material such as glyceryl monostearate may be used. When administered in solid form, such as tablet form, the solid form typically comprises from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %. Tablets may contain the active ingredients in admixture with non-toxic pharmaceutically acceptable excipients including inert materials. For example, a tablet may be prepared by compression or molding, optionally, with one or more additional ingredients. Compressed tablets may be prepared by compressing in a suitable machine the active ingredients in a free-flowing form such as powder or granules, optionally mixed with a binder, lubricant, inert diluent, surface active or dispersing agent. Molded tablets may be made by molding, in a suitable machine, a mixture of the powdered active agent moistened with an inert liquid diluent.

In some embodiments, each tablet or capsule contains from about 1 mg or less to about 1,000 mg or more of a active agent provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. In some embodiments, tablets or capsules are provided in a range of dosages to permit divided dosages to be administered. A dosage appropriate to the patient and the number of doses to be administered daily may thus be conveniently selected. In certain embodiments two or more of the therapeutic agents may be incorporated to be administered into a single tablet or other dosage form (e.g., in a combination therapy); however, in other embodiments the therapeutic agents may be provided in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents may be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, or karaya, or alginic acid or salts thereof.

Binders may be used to form a hard tablet. Binders include materials from natural products such as acacia, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, may be included in tablet formulations.

Surfactants may also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems.

Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, all of which are familiar to those skilled in the art. These devices employ formulations suitable for the dispensing of active agent. Typically, each formulation is specific to the type of device employed and may involve the use of an appropriate propellant material, in addition to diluents, adjuvants, and/or carriers useful in therapy.

The active ingredients may be prepared for pulmonary delivery in particulate form with an average particle size of from 0.1 um or less to 10 um or more, for example, from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of active agent include carbohydrates such as trehalose, mannitol, xylitol, sucrose, lactose, and sorbitol. Other ingredients for use in formulations may include DPPC, DOPE, DSPC, and DOPC. Natural or synthetic surfactants may be used, including polyethylene glycol and dextrans, such as cyclodextran. Bile salts and other related enhancers, as well as cellulose and cellulose derivatives, and amino acids may also be used. Liposomes, microcapsules, microspheres, inclusion complexes, and other types of carriers may also be employed.

Pharmaceutical formulations suitable for use with a nebulizer, either jet or ultrasonic, may comprise the active agent dissolved or suspended in water at a concentration of about 0.01 or less to 100 mg or more of active agent per mL of solution, for example, from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation may also include a buffer and a simple sugar (e.g., for protein stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device generally comprise a finely divided powder containing the active ingredients suspended in a propellant with the aid of a surfactant. The propellant may include conventional propellants, such as chlorofluorocarbons, hydrochlorofluorocarbons, hydrofluorocarbons, and hydrocarbons. Example propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing active agent, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, for example, from about 5, 10, 15, 20, 25, 30, 35, 40, 45, or 50 wt. % to about 55, 60, 65, 70, 75, 80, 85, or 90 wt. % of the formulation.

In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

In some embodiments, active agents provided herein may additionally employ adjunct components conventionally found in pharmaceutical compositions in their art-established fashion and at their art-established levels. Thus, for example, the compositions may contain additional compatible pharmaceutically active materials for combination therapy, or may contain materials useful in physically formulating various dosage forms, such as excipients, dyes, thickening agents, stabilizers, preservatives or antioxidants.

In some embodiments, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating a disease state as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of an active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Example 1

As of the effective date of this application, no therapeutics have yet been proven effective for the treatment of severe COVID-19 with cytokine storm. Ruxolitinib, a potent and selective oral inhibitor of Janus kinase (JAK) 1 and JAK2, was proposed by Applicant to be beneficial in the treatment of cytokine storm. Applicant conducted a prospective, multicenter, single-blind, randomized controlled trial involving participants diagnosed as severe COVID-19 patients. The enrolled patients were randomly separated into two groups with a 1:1 allocation by an independent statistician in blocks of 4 for all 3 sites. Study number and treatment allocation codes were provided in sequentially numbered opaque envelops. Intervention group is treated with ongoing oral intake 5 mg of ruxolitinib (Jakafi®, Novartis Pharma Stein AG, Switzerland) twice a day based on the standard-of-care (SoC); the control group is treated with placebo plus SoC. The primary endpoint was the incidence of serious adverse events occurring up to 28 days and the time to clinical improvement. The secondary endpoint is the overall mortality at $D_{28}$. This trial is registered at www.chictr.org.cn as ChiCTR-OPN-2000029580.

Forty-three patients were randomly assigned to receive ruxolitinib plus SoC treatment (22 patients) or placebo based on SoC treatment (21 patients). After exclusion of 2 patients who was ineligible or withdrew the consent in ruxolitinib group, 20 patients in intervention group and 22 patients in control group were included in safety population. No significant unexpected adverse events were observed in both groups (the primary safety endpoint). The treatment with ruxolitinib group was not associated with a difference from control group in the time to clinical improvement ((12 [IQR 10-19] days vs. 15 [IQR10-18] days, the primary efficacy endpoint). The cumulative incidence of death was compared with two groups with 14.3% of 28-day mortality in the control group (secondary endpoint).

All deaths during the observation period occurred in the control group. Patients in the ruxolitinib group had a significant shorter median time of lymphocyte recovery than those in the control group (P=0.03). Patients in the ruxolitinib group had similar median time of virus clearance compared with patients in the control group. Interestingly, the peak level of anti-IgM of SARS-CoV-2 is profoundly higher in the ruxolitinib group than in the control group (P=0.039). Patients treated with ruxolitinib had a trend of shorter median time to clinical improvement and improvement in the follow-up chest CT scans at $D_{14}$ (P=0.07). Mechanistically, the average value of 48 cytokines decreased significantly in patients of ruxolitinib group (P<0.0001), which suggested that ruxolitinib may exert its effect by targeting immune system cells, such as monocytes and macrophages, and mitigate exuberant cytokine storm in COVID-19.

Interpretation. Ruxolitinib plus SoC proved to be safe and superior in treatment of severe COVID-19. Ruxolitinib significantly mitigated exuberant cytokine storm featured in severe COVID-19, and statistical significance (p=0.05) was achieved for primary efficacy endpoint.

Infections of COVID-19 and other coronaviruses, such as SARS-CoV and MERS, etc, are associated with an exuberant cytokine storm[14-18]. Upon virus infection, individuals respond by eliciting inflammatory cytokines to activate appropriate immune responses, restrict spread/replication of the virus and eliminate the virus eventually. However, highly pathogenic coronaviruses often induce uncontrolled cytokine/chemokine response known as cytokine storms, which results in high morbidity and mortality due to immunopathology[19]. This is especially obvious in those individuals with underlying diseases. While virus-induced direct pathogenic effects play an important role in disease severity, viral load of individuals with SARS is not correlated with the worsening of symptoms[4,20,21]. Studies from individuals who died of SARS suggest that a dysregulated immune response occurred, which results in an exuberant inflammation and lethal disease[22]. In a recent report of 41 cases of confirmed COVID-19, one third of patients were admitted to ICUs with 10% of patients needing mechanical ventilation, and six died (14.6%), of which cytokine storm was found to be associated with disease severity[4]. Although the cellular tropism of SARS-CoV-2 is limited, severe dysfunctions and damages can occur in the hearts, kidneys, brains and many other organs in severe/critical COVID-19 patients. There is accumulating evidence on the key pathophysiological role of cytokines during the most severe stage of COVID-19. Against the backdrop of a lack of vaccine and specific antiviral agents, increasing interest in testing immunomodulatory agents has been proposed to reduce excessive or uncontrolled inflammation to before it overwhelmingly results in irreversible multi-organ dysfunction infection.

Ruxolitinib is a first-in-class Janus-associated kinase (JAK1/2) inhibitor approved by the U.S. Food and Drug Administration (FDA) and European Medicines Agency for the treatment of polycythemia vera and myelofibrosis patients in adults[23]. It is also a promising option for treating steroid-refractory acute graft-versus-host disease (SR-aGVHD) after allogeneic hematopoietic stem cell transplantation (allo-HSCT)[24,25] or secondary hemophagocytic lymphohistiocytosis[26,27] by targeting the deleterious effects of aberrant host inflammatory response. Applicant hypostasized that ruxolitinib may be effective against the consequences of the elevated levels of cytokines typically observed in severe/critical COVID-19 patients. To evaluate the safety and efficacy of ruxolitinib for COVID-19, Applicant conducted a randomized, multicenter, placebo-controlled, single-blind trial in patients hospitalized with severe COVID-19 as follows.

A prospective, single-blind, randomized controlled trial was designed. Participants diagnosed as positive for COVID-19 were enrolled for screening in three hospitals including Tongji hospital and No. 1 hospital in Wuhan and the Third Xiangya hospital in Changsha, China. The original protocol included secondary randomization in a treatment group for infusion of mesenchymal stem cells if the patient's clinical response had deteriorated within seven days after first randomization. Because no deterioration had occurred in patients of the treatment group within seven days after first randomization and secondary randomization was unnecessary, the protocol was updated correspondingly. This study was approved by the Medical ethics committee of Tongji Hospital, Tongji Medical College, Huazhong University of Science and Technology, Wuhan, China, registered at www.chictr.org.cn as ChiCTR-OPN-2000029580.

Sample collection. Serum samples were collected using a serum separator tube (SST) and samples were allowed to clot for 30 minutes at room temperature before centrifuging for 15 minutes at 1000×g. Serum and assay were removed immediately or aliquoted and stored at ≤−20° C. Repeated freeze-thaw cycles were avoided. Plasma samples were collected using EDTA or heparin as an anticoagulant and centrifuged for 15 minutes at 1000×g. Assay was used immediately or aliquoted and stored at ≤−20° C., again avoiding repeated freeze-thaw cycles.

Determination of SARS-CoV-2 copies number by One-step RT-ddPCR. For quantitative detection of SARS-CoV-2 copy number, Viral RNA purification kit (QlAamp Viral RNA Mini Kit, Qiagen, Germany), one-step RT-ddPCR advanced kit, QX200 droplet generator (BioRad, USA) and QX200 droplet reader (BioRad, USA) were used following the manufacturer's instructions. To increase sensitivity, a 4-well test was performed per sample in this study. The SARS-CoV-2 specific minor groove binder (MGB) probe-primer set was designed for targeting the orf1ab region and the sequences were as follows: forward primer 5'TGA CCC TGT GGG TTT TAC ACT TAA3' (SEQ ID NO 1); reverse primer 5'CAGCCATAACCTTTCCACATACC3'(SEQ ID NO 2); probe 5'-FAM-AAC ACA GTC TGT ACC GTC T(SEQ ID NO 3)-MGB—3'.

SARS-CoV-2-specific IgM and IgG detection. The SARS-CoV-2-specific IgM and IgG were detected by paramagnetic particle chemiluminescent immunoassay (CLIA) using iFlash-SARS-CoV-2 IgM/IgG assay kit (SHENZHEN YHLO BIOTECH CO., LTD.) and iFlash Immunoassay Analyzer (SHENZHEN YHLO BIOTECH CO., LTD.)

Cytokines measurements and analysis. The levels of serum cytokines, growth factors and chemokines were assessed by Bio-Plex Pro Human Cytokines 48-Plex Screening assay (Bio-Rad Life Sciences) using a Luminex FlEX-MAP 3D system according to the manufacturer's protocols. The 48-Plex Screening panel is as follows: Basic FGF, CTACK, eotaxin, G-CSF, GM-CSF, GRO-α, HGF, ICAM-1, IFN-α2, IFN-γ, IL-1α, IL-1rα, IL-2, IL-2Ra, IL-3, IL-4, IL-5, IL-6, IL-7, IL-8, IL-9, IL-10, IL-12, IL-13, IL-15, IL-16, IL-17A, IL-18, IP-10, LIF, MCP-1, MCP-3, M-CSF, MIF, MIG, MIP-1α, MIP-1β,β-NGF, PDGF-BB, RANTES, SCF, SCGF-β, SDF-1α, TNF-α, TNF-β, TRAIL, VCAM-1, VEGF-A Participants. All participants were required to meet the following inclusion criteria: (1) enrolled patients met the diagnostic criterial for COVID-19. The diagnosis and the illness severity of COVID-19 were defined according to the Chinese management guideline for COVID-19 (version 5.0)[28]; (2) patients were eligible if they were 18 years or older and younger than 75 years. (3) only severe cases were enrolled. Exclusion criterial included: (1) patients with other malignant tumors in the course of treatment; (2) patients with severe cardiovascular and metabolic disease in unstable status, even if treated with drugs; (3) patients with mental or severe psychiatric disorder who are unable to understand or abide the study protocols; (4) patients needing orotracheal intubation or invasive ventilation; (5) patients who cannot guarantee to complete the scheduled treatment plan and follow-up; (6) women of child-bearing age having positive pregnancy test or still lactating; (7) patients having other active infections; (8) patients having any conditions deemed to potentially affect the safety of the study protocols. Written informed consent was obtained from all patients or the patients' legal representative if the patient was too unwell to provide the consent.

Randomization and masking. The enrolled patients were then randomly allocated into two groups with a 1:1 allocation ratio by an independent statistician using permuted blocks of 4 for all 3 sites. Patient unique identification number and treatment allocation codes were provided in sequentially numbered opaque envelops. Treating physicians were aware of group allocations while the enrolled participants, staff at trial sites, CT radiologists and laboratory personnel were masked to the trial group assignment.

Procedures. The first day of randomization was designated as $D_0$. The second and the fourth day after randomization were designated $D_1$ and $D_3$, respectively. $D_x$ referred to the day when either disease progressed according to the Chinese management guideline for COVID-19 (version 5.0) or defined as a one-category increase on the seven-category scale. $D_{end}$ was the day before discharge. The enrolled patients were randomly separated into two groups: the treatment group (group B) received oral intake of ruxolitinib (Jakafi®, Novartis Pharma Stein AG, Switzerland) 5 mg twice a day plus standard-of-care (SoC); the control group (group A) is treated with placebo twice a day with SoC. The SoC included supplemental oxygen, noninvasive and invasive ventilation, corticosteroid, antibiotic agents, vasopressor support, renal-replacement therapy, and extracorporeal membrane oxygenation (ECMO) etc. Safety was monitored daily by two independent senior physicians from the trial center. Adverse events were classified according to the National Cancer Institute Common Terminology Criteria for Adverse Events, version 5.0. Non-contrast enhanced chest CT examinations were performed on $D_0$ and followed-up at least once within two weeks. Additional chest CT may be performed if the condition deteriorated. All CT images were reviewed using Picture archiving and communication system (PACS). The CT features of improvement were evaluated by two independent senior radiologists blindly, which should at least meet one of the following criteria: decreased presence of ground-glass opacities (GGO), decreased lung opacification, reduced density of consolidation or decreased pleural effusion with existence of fibrous stripes[29]. Peripheral blood was taken from patients on $D_1$, $D_3$, $D_x$ and/or $D_{end}$ for the determination of viral load by one-step RT-ddPCR, SARS-CoV-2-specific IgM and IgG by paramagnetic particle chemiluminescent immunoassay (CLIA) and cytokines measurements by Luminex FlEXMAP 3D system. Every participant's data is filled in one case record form (CRF). All the CRF tables were inputted and saved by researchers into an electronic data capture system (EDCS) and validated by a trial staff, including demographics, medical history, daily clinical findings, oximetric measurements and laboratory data involving complete blood count, serum biochemical parameters and high sensitivity C-reactive protein (hsCRP) etc.

Outcomes. The primary safety endpoint was the incidence of serious adverse events occurring up to 28 days. Safety outcomes included adverse events that occurred during treatment, serious adverse events and premature discontinuation of treatment. The primary efficacy end point was the time to clinical improvement, defined as the time from randomization ($D_0$) to an improvement of two points on a seven-category ordinal scale or live discharge from the hospital ($D_{end}$). The seven-category ordinal scale was used in other COVID-19 RCT trials[12] and recommended by the WHO R&D Blueprint expert group[30]. It consisted of following criteria: 1, not hospitalized with resumption of normal activities; 2, not hospitalized, but unable to resume normal activities; 3, hospitalized, not requiring supplemental oxygen; 4, hospitalized, requiring supplemental oxygen; 5, hospitalized, requiring nasal high-flow oxygen therapy, noninvasive mechanical ventilation, or both; 6, hospitalized, requiring ECMO, invasive mechanical ventilation, or both; and 7, death. Other clinical outcomes included clinical improvement rate as assessed with the seven-category ordinal scale on $D_7$, $D_{14}$, $D_{21}$ and $D_{28}$, or as assessed with follow-up CT scans within two weeks, the duration of randomization to lymphocyte recovery and to mechanical ventilation, the duration of hospitalization in survivors, and the time (in days) from treatment initiation to death and virus clearance time. Lymphocyte recovery time was defined as the first day that lymphocytes consecutively return to the normal level within observation period. The virus clearance time is defined as the time from randomization to the first day of at least 2 consecutive negative RT-PCR assays separated by 24 h apart. The secondary endpoint is the overall mortality at $D_{28}$. The investigational outcomes included the dynamic changes of the virus copies, cytokine profile, SARS-CoV-2-specific antibody and its correlation with clinical treatment response.

Statistical analysis. The trial was initiated in rapid response to COVID-19 public health emergency, and limited information about clinical outcomes in hospitalized patients with COVID-19 were available at that time. The estimated sample size was set at 40 to provide the trial with 80% power to detect a 40% difference in term of CT improvement within 14 days after randomization between the two groups assuming that approximately 50% patients in group A. The planned enrollment of 40 patients in the trial occurred quickly. The assessment at that point was that the trial was underpowered. Because newly diagnosed patients decreased with gradual recovery of pandemics at the end of February in Wuhan, China and therefore principle investigator decided to suspend the enrollment.

Continuous variables were expressed as median (IQR) and compared with the unpaired 2-sided student's t test; categorical variables were expressed as number (%) and compared by χ2 test or Fisher's exact test. For primary endpoint, the time to clinical improvement was compared with a log-rank test. The improvement rate of CT scan at $D_{14}$, clinical improvement at $D_7$, $D_{14}$ and $D_{21}$ were compared using Kaplan-Meier method by a log-rank test. Time from randomization to discharge, to death, to lymphocyte recovery, and to virus clearance time were compared using the Fisher's exact tests. For comparing cytokines, anti-SARS-CoV-2 specific antibody and virus copy numbers, mean±SEM is given for continuous variables, median and ranges are given for variables that were not normally distributed. Means were compared using t tests for normally distributed continuous variable. Otherwise, the Mann-Whitney U test was used. All statistical analyses were performed using SPSS (Statistical Package for the Social Science) version 13.0 software (SPSS Inc.). P values less than 0.05 (two-tailed) were statistically significant.

Results. Of 58 individuals screened for eligibility, 43 patients were randomly assigned to receive ruxolitinib plus SoC treatment (22 patients, ruxolitinib group) or placebo based on SoC treatment (21 patients, control group). After randomization, two patients were excluded from ruxolitinib group since one was found to be ineligible because of persistent humoral immune deficiency post B cell mature antigen (BCMA) targeting chimeric antigen receptor (CAR) T cell therapy and another withdrew the consent before treatment start (FIG. 1). Their clinical data were not included in the analyses. The demographic and clinical characteristic of the patients at baseline is outlined in Table 1. At baseline, the median age of patients was 63 years (interquartile range [IQR], 58 to 68 years), ranging from 32 years to 75 years, and 58.5% of the patients were men. The median interval time from symptom onset to randomization was 20 days. No relevant differences between two groups in demographic characteristics, baseline laboratory test result, distribution of ordinal scale scores, or National Early Warning Score 2 (NEWS2) scores at enrollment were noted (Table 1 and Table 2). During the study, the use of systemic corticosteroid was balanced between ruxolitinib group (70.0%) and control group (71.4%). The proportion of patients received antivirals were balanced between two groups (90.0% in ruxolitinib group vs. 90.5% in control group) (Table 2).

TABLE 1

Demographic and Clinical Characteristic of the Patients at Baseline.

| Characteristic | Total N = 41 | Control group N = 21 | Ruxolitinib group N = 20 |
|---|---|---|---|
| Age, years | 63 (58-68) | 64 (59-71) | 63 (51-65) |
| Sex | | | |
| Female | 17 (41.5%) | 9 (42.9%) | 8 (40.0%) |
| Male | 24 (58.5%) | 12 (57.1%) | 12 (60.0%) |
| Comorbidity | | | |
| Hypertension | 16 (39.0%) | 9 (42.9%) | 7 (35.0%) |
| Diabetes | 8 (19.5%) | 3 (14.3%) | 5 (25.0%) |
| Coronary artery heart disease | 3 (7.3%) | 1 (4.8%) | 2 (10.0%) |
| Smoking history | 4 (9.8%) | 2 (9.5%) | 2 (10.0%) |
| Respiratory rate >24 breaths per min | 8 (19.5%) | 4 (19.0%) | 4 (20.0%) |
| Pulse ≥ 125 beats per min | 7 (17.1%) | 3 (14.3%) | 4 (20.0%) |
| Fever (temperature ≥ 37·3° C.) | 5 (12.2%) | 2 (9.5%) | 3 (15.0%) |
| White-cell count, ×10⁹ per L | 8.4 (6.1-11.0) | 8.3 (6.7-11.0) | 8.4 (5.6-11.0) |
| <4 | 2 (4.9%) | 0 (0.0%) | 2 (10.0%) |
| 4-10 | 26 (63.4%) | 14 (66.7%) | 12 (60.0%) |
| >10 | 13 (31.7%) | 7 (33.3%) | 6 (30.0%) |
| Lymphocyte count, ×10⁹ per L | 1.1 (0.92-1.6) | 1.2 (0.97-2.0) | 1.0 (0.8-1.2) |
| ≥1.0 | 25 (61.0%) | 15 (71.4%) | 10 (50.0%) |
| <1.0 | 16 (39.0%) | 6 (28.6%) | 10 (50.0%) |
| Platelet count | 264 (173-314) | 214 (175-285) | 297 (165-355) |
| ≥100 | 36 (87.8%) | 19 (90.5%) | 17 (85.0%) |
| <100 | 5 (12.2%) | 2 (9.5%) | 3 (15.0%) |
| Serum creatinine, μmol/L | 67 (56-75) | 66 (60-74) | 69 (52-75) |
| ≤133 | 38 (92.7%) | 20 (95.2%) | 18 (90.0%) |
| >133 | 3 (7.3%) | 1 (4.8%) | 2 (10.0%) |
| Aspartate aminotransferase, U/L | 36 (23-68) | 35 (19-88) | 39 (26-52) |
| ≤40 | 24 (58.5%) | 13 (61.9%) | 11 (55.0%) |
| >40 | 17 (41.5%) | 8 (38.1%) | 9 (45.0%) |
| Alanine aminotransferase, U/L | 25 (17-46) | 23 (18-50) | 26 (17-47) |

TABLE 1-continued

Demographic and Clinical Characteristic of the Patients at Baseline.

| Characteristic | Total N = 41 | Control group N = 21 | Ruxolitinib group N = 20 |
|---|---|---|---|
| ≤50 | 30 (73.2%) | 15 (71.4%) | 15 (75.0%) |
| >50 | 11 (26.8%) | 6 (38.6%) | 5 (25.0%) |
| Lactate dehydrogenase, U/L | 275 (225-413) | 300 (226-438) | 262 (213-384) |
| ≤245 | 16 (39.0%) | 8 (38.1%) | 8 (40.0%) |
| >245 | 25 (61.0%) | 13 (61.9%) | 12 (60.0%) |
| Albumin, g/L | 32 (30.0-34.0) | 32.0 (30.0-34.0) | 32.0 (30.0-35.0) |
| ≤35 | 32 (78.0%) | 17 (81.0%) | 15 (75.0%) |
| >35 | 9 (22.0%) | 4 (19.0%) | 5 (25.0%) |
| D-Dimer, μg/mL | 2.4 (0.65-7.5) | 2.5 (0.68-15.0) | 2.1 (0.62-3.5) |
| ≤1.0 | 14 (34.1%) | 6 (28.6%) | 8 (40.0%) |
| >1.0 | 23 (56.1%) | 13 (61.9%) | 10 (50.0%) |
| Missing data | 4 (9.8%) | 2 (9.5%) | 2 (10.0%) |
| High-sensitive cardiac troponin I, ng/mL | 3.5 (2.0-6.3) | 3.0 (1.6-6.8) | 4.1 (2.2-6.5) |
| ≤28.0 | 33 (80.5%) | 18 (85.7%) | 15 (75.0%) |
| >28.0 | 5 (12.2%) | 2 (9.5%) | 3 (15.0%) |
| Missing data | 3 (7.3%) | 1 (4.8%) | 2 (10.0%) |

Data are median (IQR) or n (%)

TABLE 2

Patients' Status and Treatments Received at or after Enrollment.

| Characteristic | Total N = 41 | Control group N = 21 | Ruxolitinib group N = 20 |
|---|---|---|---|
| NEWS2 score at day 1 | 5 (4-6) | 4 (4-5) | 5 (4-7) |
| Days from illness onset to randomization | 20 (17-28) | 22 (18-28) | 20 (16-27) |
| Seven-category scale at day 1 | | | |
| 4: Hospitalization, requiring supplemental oxygen | 35 (85.4%) | 17 (81.0%) | 18 (90.0%) |
| 5: Hospitalization, requiring HFNC or noninvasive mechanical ventilation | 5 (12.2%) | 3 (14.3%) | 2 (10.0%) |
| Treatments during study period | | | |
| Vasopressor | 3 (7.3%) | 3 (14.3%) | 0 |
| Noninvasive mechanical ventilation | 7 (17.1%) | 5 (23.8%) | 2 (10.0%) |
| Invasive mechanical ventilation | 3 (7.3%) | 3 (14.3%) | 0 |
| Glucocorticoid therapy | 29 (70.7%) | 15 (71.4%) | 14 (70.0%) |
| Renal-replacement therapy | 2 (48.8%) | 2 (9.5%) | 0 |
| Intravenous Immunoglobin | 18 (43.9%) | 11 (52.4%) | 7 (35.0%) |
| Antibiotic agent | 20 (48.8%) | 12 (57.1%) | 8 (40.0%) |
| Antiviral agent | 37 (90.2%) | 19 (90.5%) | 18 (90.0%) |

Data are median (IQR) or n (%); HFNC denotes high-flow nasal cannula for oxygen therapy and NEWS2 National Early Warning Score 2.

For primary safety endpoint, a total of 16 patients (80%) in ruxolitinib group and 15 patients (71.4%) in the control group reported adverse events from randomization to $D_{28}$. The hematological adverse events including neutropenia, lymphopenia, anemia and thrombocytopenia were more common in ruxolitinib group, however, only 1 (5%) patient in control group developed serious hematological toxicity (Grade 3 or 4) compared with 2 (9.6%) patients in ruxolitinib group. Patients with serum biochemical abnormalities were of low grade (Grade 1~2) and the percentages of which in ruxolitinib group showed mildly higher than in control group. However, no significant differences were found between the two groups. One patient in ruxolitinib group developed Grade 3 hypertension during the study but transient and reversible. Serious adverse events including secondary infection, sepsis, shock and acute heart failure occurred in 4 patients in control group rather than in ruxolitinib group. All 4 events were judged by the investigators to be related to the trial medication. All deaths during the observation period occurred in control group (Table 3).

TABLE 3

Summary of Adverse Events. Adverse events that occurred in more than 1 patient after randomization through day 28 are shown. Some patients had more than one adverse event. The proportions of patients with values worse than baseline values are listed here. All deaths were due to respiratory failure.

| | Control group (N = 21) | | | Ruxolitinib group (N = 20) | | |
|---|---|---|---|---|---|---|
| | Any Grade | Grade 1-2 | Grade 3-4 | Any Grade | Grade 1-2 | Grade 3-4 |
| Hematological adverse events | 12 (57.2%) | 10 (47.6%) | 2 (9.6%) | 13 (65.0%) | 12 (60.0%) | 1 (5.0%) |
| Neutrocytopenia | 1 (4.8%) | 1 (4.8%) | 0 | 1 (5.0%) | 1 (5.0%) | 0 |
| Lymphocytopenia | 4 (19.0%) | 3 (14.3%) | 1 (4.8%) | 1 (5.0%) | 1 (5.0%) | 1 (5.0%) |

TABLE 3-continued

Summary of Adverse Events. Adverse events that occurred in more than 1 patient after randomization through day 28 are shown. Some patients had more than one adverse event. The proportions of patients with values worse than baseline values are listed here. All deaths were due to respiratory failure.

|  | Control group (N = 21) | | | Ruxolitinib group (N = 20) | | |
| --- | --- | --- | --- | --- | --- | --- |
|  | Any Grade | Grade 1-2 | Grade 3-4 | Any Grade | Grade 1-2 | Grade 3-4 |
| Anemia | 9 (42.9%) | 8 (38.1%) | 1 (4.8%) | 11 (55.0%) | 11 (55.0%) | 0 |
| Thrombocytopenia | 3 (14.3%) | 2 (9.6%) | 1 (4.8%) | 4 (20.0%) | 4 (20.0%) | 0 |
| Chemical laboratory abnormalities | 7 (33.3%) | 7 (33.3%) | 0 | 10 (50.0%) | 10 (50.0%) | 0 |
| ALT increase | 2 (9.6%) | 2 (9.6%) | 0 | 7 (35.0%) | 7 (35.0%) | 0 |
| AST increase | 1 (4.8%) | 1 (4.8%) | 0 | 3 (15.0%) | 3 (15.0%) | 0 |
| Alkaline phosphatase increase | 1 (4.8%) | 1 (4.8%) | 0 | 2 (10.0%) | 2 (10.0%) | 0 |
| γ-GT increase | 2 (9.6%) | 2 (9.6%) | 0 | 2 (10.0%) | 2 (10.0%) | 0 |
| Hypoalbuminemia | 3 (14.3%) | 3 (14.3%) | 0 | 1 (5.0%) | 1 (5.0%) | 0 |
| Hypercholerolemia | 4 (19.0%) | 4 (19.0%) | 0 | 4 (20.0%) | 4 (20.0%) | 0 |
| Hypertriglyceridemia | 2 (9.6%) | 2 (9.6%) | 0 | 0 | 0 | 0 |
| Hypokalemia | 1 (4.8%) | 1 (4.8%) | 0 | 1 (5.0%) | 1 (5.0%) | 0 |
| Hypochloremia | 2 (9.6%) | 2 (9.6%) | 0 | 1 (5.0%) | 1 (5.0%) | 0 |
| Hypocalcemia | 2 (9.6%) | 2 (9.6%) | 0 | 1 (5.0%) | 1 (5.0%) | 0 |
| Adverse events | 6 (28.6%) | 6 (28.6%) | 0 | 7 (35.0%) | 7 (35.0%) | 0 |
| Headache | 0 | 0 | 0 | 1 (5.0%) | 1 (5.0%) | 0 |
| Dizziness | 1 (4.8%) | 1 (4.8%) | 0 | 2 (10.0%) | 2 (10.0%) | 0 |
| Rash | 1 (4.8%) | 1 (4.8%) | 0 | 2 (10.0%) | 2 (10.0%) | 0 |
| Nausea | 2 (9.6%) | 2 (9.6%) | 0 | 2 (10.0%) | 2 (10.0%) | 0 |
| Decreased appetite | 2 (9.6%) | 2 (9.6%) | 0 | 1 (5.0%) | 1 (5.0%) | 0 |
| Hypertension | 2 (9.6%) | 2 (9.6%) | 0 | 1 (5.0%) | 0 | 1 (5.0%) |
| Serious adverse events | 4 (19.0%) | 0 | 4 (19.0%) | 0 | 0 | 0 |
| Secondary Infection | 2 (9.6%) | 0 | 2 (9.6%) | 0 | 0 | 0 |
| Acute heart failure | 2 (9.6%) | 0 | 2 (9.6%) | 0 | 0 | 0 |
| Shock | 2 (9.6%) | 0 | 2 (9.6%) | 0 | 0 | 0 |
| Sepsis | 1 (4.8%) | 0 | 1 (4.8%) | 0 | 0 | 0 |

Figure 2:
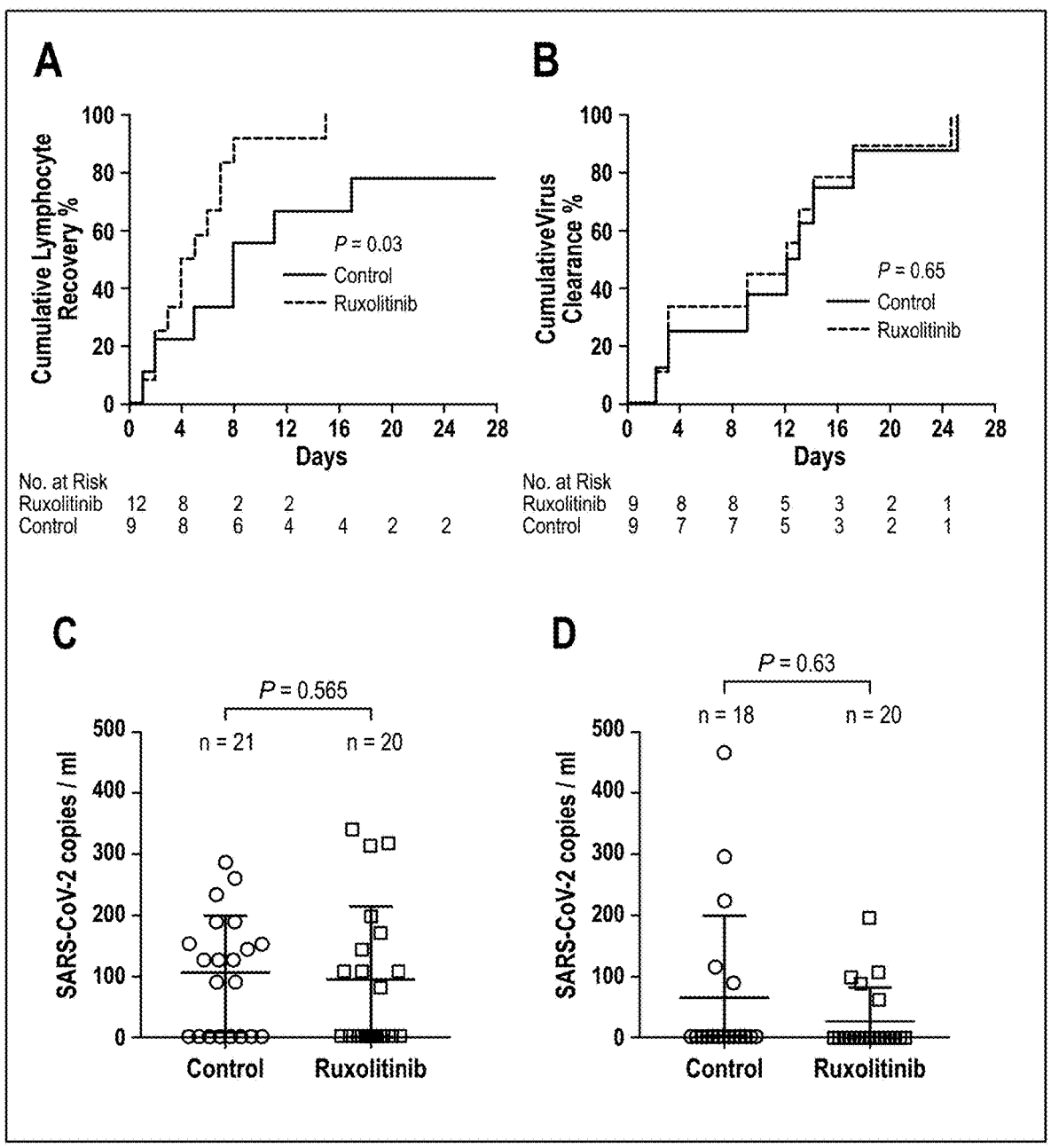
FIG. 2. Primary and Secondary outcomes. (A) Cumulative incidence of lymphocyte recovery rate in modified intention-to-treat analysis patients. (B) Cumulative incidence of virus clearance rate in modified intention-to-treat analysis patients. (C) Comparison of blood viral loads of control group and ruxolitinib group at D1. (D) Comparison of blood viral loads of control group and ruxolitinib group at discharge. (E-F) The peak levels of SARS-CoV-2 specific IgM (E), IgG (F). (G) The cumulative improvement rate in modified intention-to-treat analysis patients. (H) Cumulative 28 days incidence of death.
Figure 2:
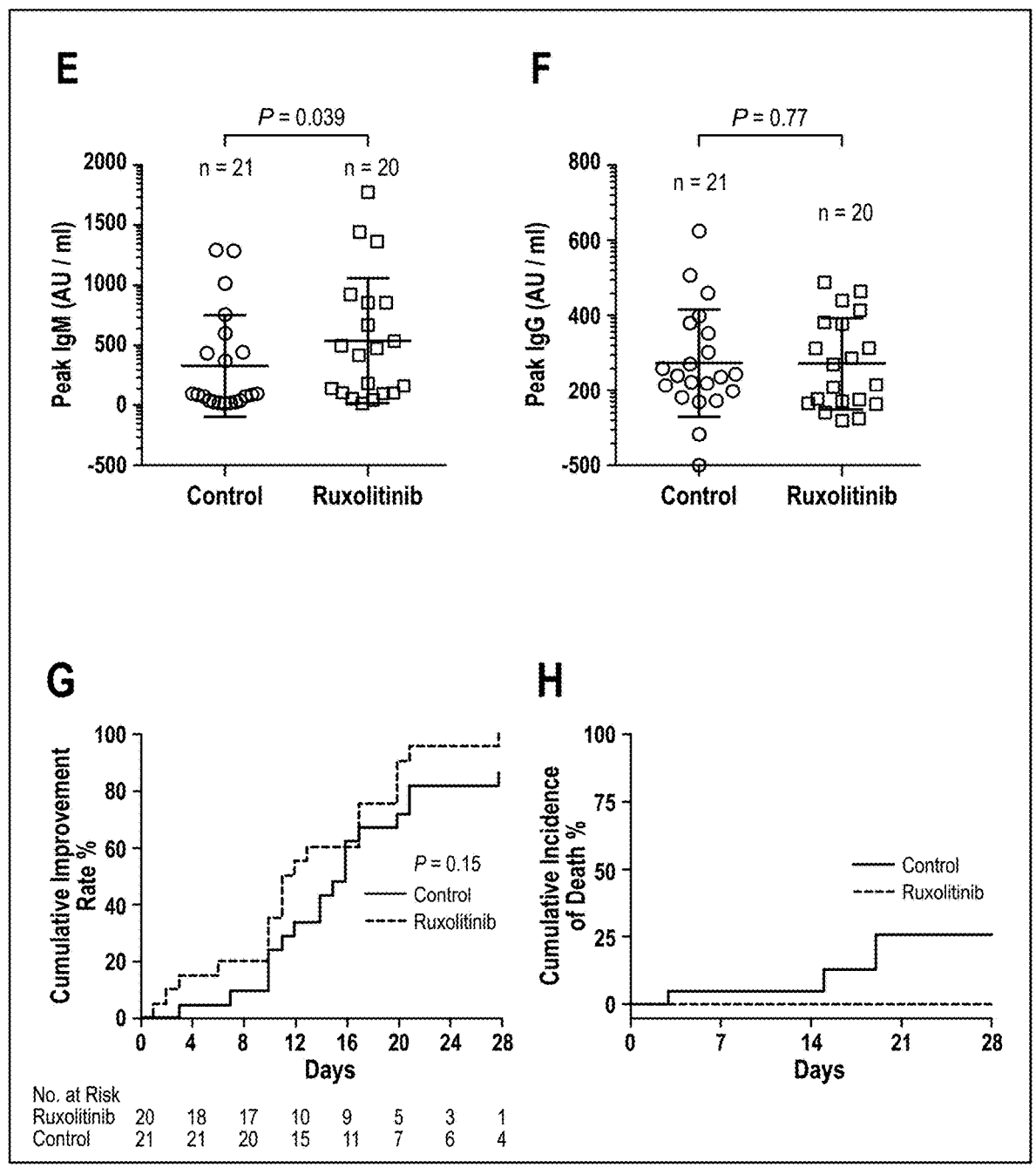

A total of 21 patients (9 patients in control group and 12 patients in ruxolitinib group) were found to have lymphopenia at or after enrollment. However, patients in ruxolitinib group had a significant shorter median time of lymphocyte recovery than those in control group. (FIG. 2A: 5 [IQR 2-7] days vs. 8 [IQR 2-11] days, log-rank test P=0.03). To address the concern that ruxolitinib may influence SARS-CoV-2 clearance, a total of 17 patient (8 patients in ruxolitinib group and 9 patients in control group) who had a positive RT-PCR result on the throat swab were serially followed up. Patients in the ruxolitinib group had similar median time of virus clearance (13 [IQR 5-16] days vs 12 [IQR 3-16] days, log-rank test P=0.65) compared with patients in control group (FIG. 2B). One step RT-ddPCR was also used to further evaluate the clearance of SARS-CoV-2, the mean (±SEM) baseline blood viral RNA loads at $D_1$ in ruxolitinib group were comparable with control group (FIG. 2C, 94±26 copies per milliliter vs 102±21, P=0.57). The viral load at discharge did not differ between the ruxolitinib recipients and those receiving SoC alone. (FIG. 2D, P=0.63). Interestingly, the peak level of anti-IgM of SARS-CoV-2 is profoundly higher in the ruxolitinib group than in the control group (P=0.039), while no significant difference was found in peak IgG between the two groups. (FIG. 2E-F). Thus, ruxolitinib may be used to help the humoral immune response, specifically IgM. While there was a trend for early virus clearance, it did not reach statistical significance with this sample.

For primary efficacy endpoint, patients treated with ruxolitinib group had a trend of shorter median time to clinical improvement (12 [IQR 10-19] days vs. 15 [IQR10-18] days, log-rank test P=0.15) compared with those treated with control group (Table 4, FIG. 2G). Consistent with the findings, 18 (90%) patients in the ruxolitinib group showed improvement in the follow-up chest CT scans at $D_{14}$ compared with 13 (61.9%) patients in control group (P=0.07) (Table 4).

TABLE 4

Outcomes in the enrolled patients, Data are median (IQR) or n (%)

| Characteristic | Total N = 41 | Control group N = 21 | Ruxolitinib group N = 20 | P |
| --- | --- | --- | --- | --- |
| Clinical improvement | | | | |
| Day 7 | 6 (14.6%) | 2 (9.5%) | 4 (20.0%) | 0.41 |
| Day 14 | 21 (51.2%) | 9 (42.9%) | 12 (60.0%) | 0.35 |
| Day 21 | 36 (87.8%) | 18 (85.7%) | 18 (90.0%) | 1.00 |
| Day 28 | 38 (92.7%) | 18 (85.7%) | 20 (100.0%) | 0.23 |
| Time to clinical improvement, d | 14 (10-18) | 15 (10-18) | 12 (10-19) | 0.15 |
| Clinical deterioration | | | | |
| Day 7 | 3 (7.3%) | 3 (14.3%) | 0 | 0.23 |
| Day 14 | 4 (9.8%) | 4 (19.0%) | 0 | 0.11 |

TABLE 4-continued

Outcomes in the enrolled patients, Data are median (IQR) or n (%)

| Characteristic | Total N = 41 | Control group N = 21 | Ruxolitinib group N = 20 | P |
|---|---|---|---|---|
| Time to clinical deterioration, d | | 6 (2-12) | | |
| CT scan follow-up within 14 days | | | | 0.07 |
| Improvement | 31 (75.6%) | 13 (61.9%) | 18 (90.0%) | |
| Stable | 7 (17.1%) | 6 (28.6%) | 1 (5.0%) | |
| Progression | 3 (7.3%) | 2 (9.5%) | 1 (5.0%) | |
| Day 28 mortality | 3 (7.3%) | 3 (14.3%) | 0 | 0.23 |
| Time from randomization to discharge, d | 16 (11-20) | 16 (11-20) | 17 (11-21) | 0.94 |
| Duration of invasive mechanical ventilation, d | | 6 (3-9) | | |
| Time from randomization to death, d | 16 (4-20) | 16 (4-20) | 0 | |
| Time to lymphocyte recovery, d | 6 (3-10) | 8 (4-18) | 5 (2-7) | 0.03 |
| Virus clearance time, d | 12 (3-16) | 12 (3-16) | 13 (5-16) | 0.85 |

The clinical improvement percentage of patients was numerically higher at $D_7$, $D_{14}$ and $D_{21}$ in ruxolitinib group than in control group. However, no significant difference was observed between two groups. A total of 3 patients in control group at $D_7$ and 4 patients at $D_{14}$ experienced clinical deterioration. Three patients were transferred to the ICU and required intubation and mechanical ventilation. The cumulative improvement rate was compared with two groups (FIG. 2A).

For secondary endpoint, 3 patients in the control group eventually died of respiratory failure. The 28-day overall mortality was 14.3% in the control group. None in the ruxolitinib group died. The median time from randomization to death was 16 days (4~20) in control group. There was no significant difference in the days from randomization to discharge between two groups (P=0.94). The cumulative incidence of death was compared with two groups (FIG. 2H).

Figure 3:
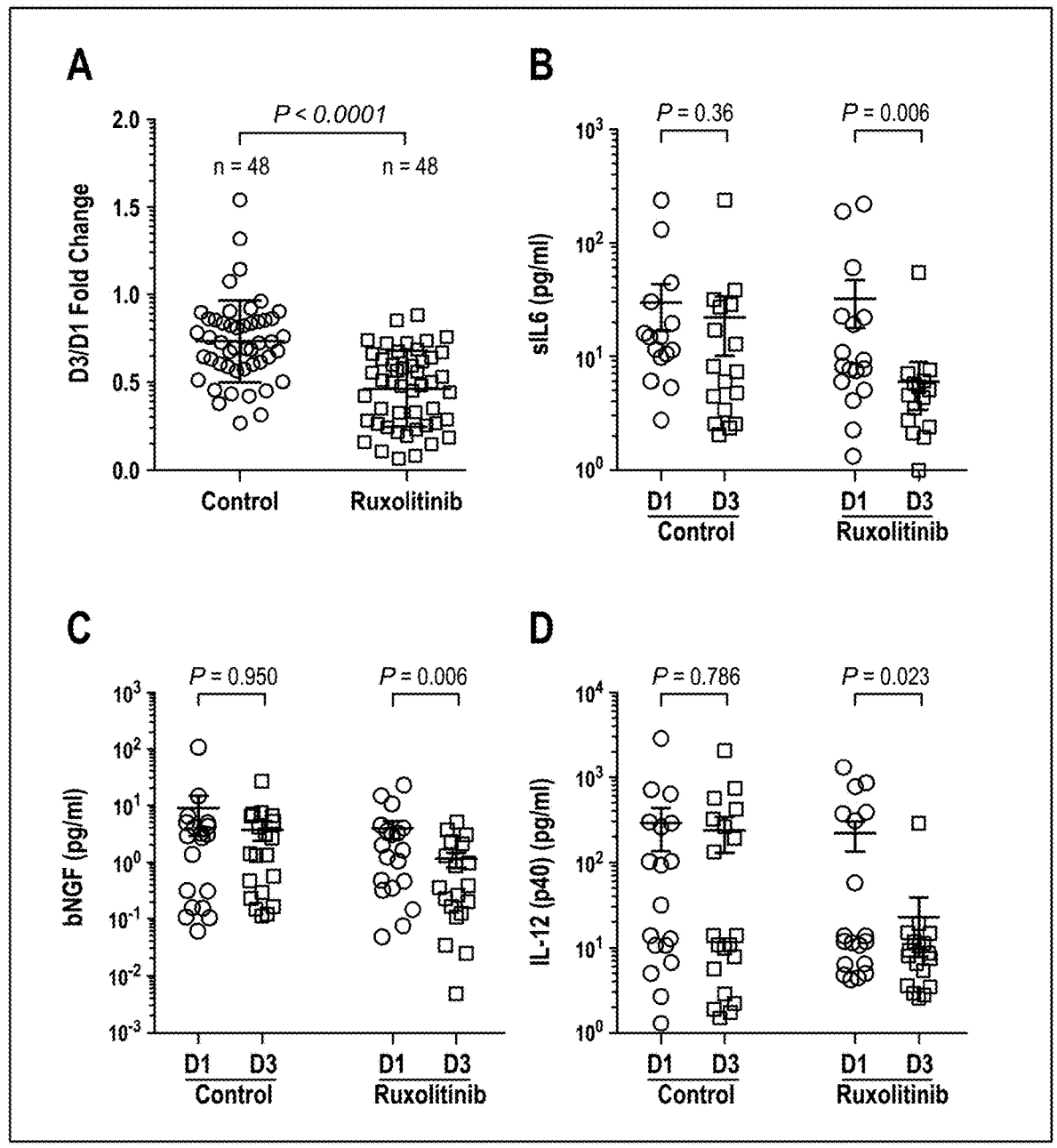
FIG. 3. Serial cytokine assessment of 48 cytokines was performed in ruxolitinib group and control group. (A) Ratio of mean value of each cytokine at D3 and D1 after randomization. (B-H) Stacked scatter plots demonstrated cytokines which were significantly decreased in ruxolitinib group. All data represent mean±SEM.
Figure 3:
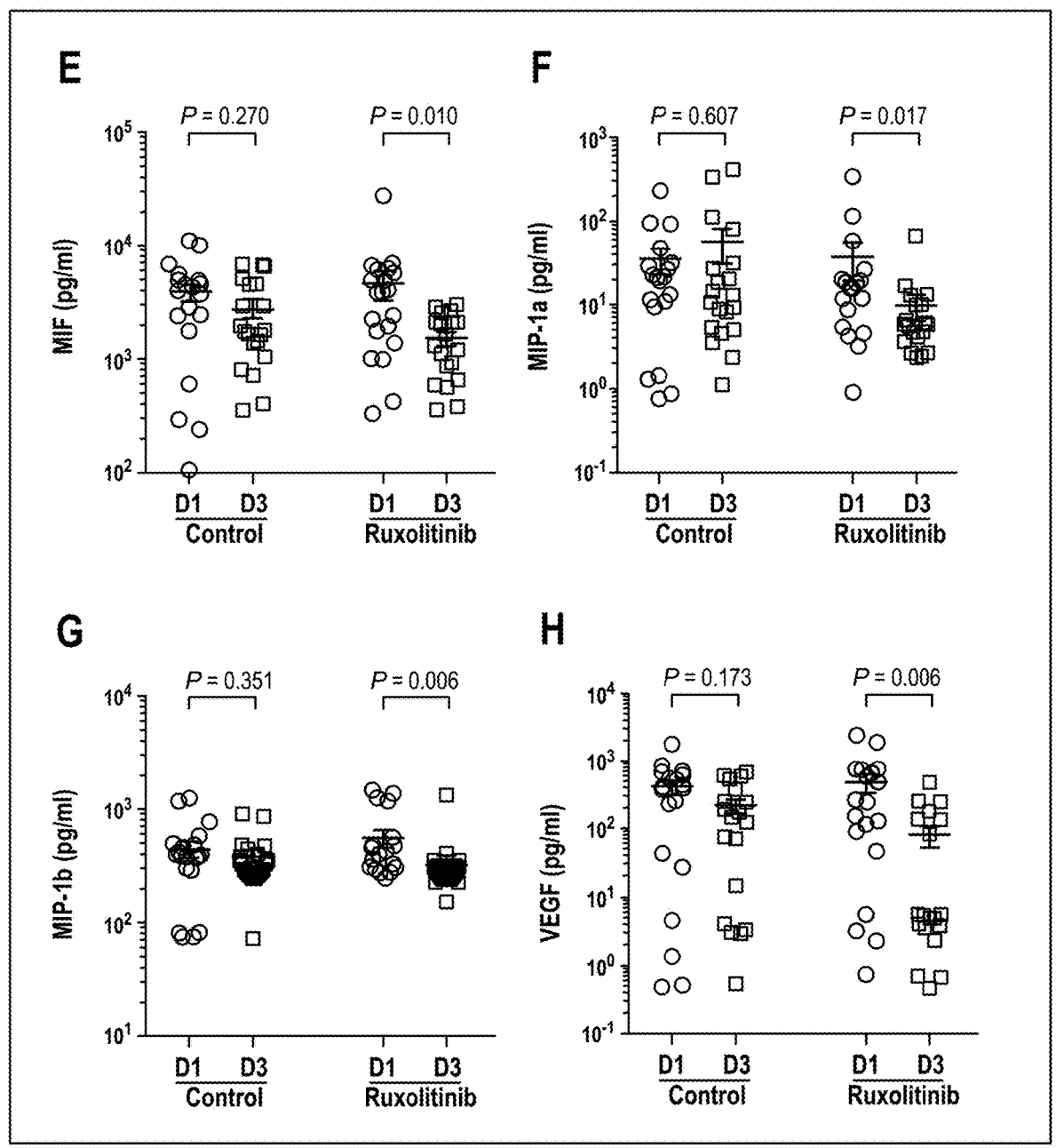

JAKs mediate signals from a variety of cytokines and growth factors. Ruxolitinib is a JAK inhibitor with selectivity for JAK1 and JAK2. To address whether ruxolitinib could inhibit cytokines downstream of JAKs, Applicant assessed the levels of 48 cytokines in serum of patients who received ruxolitinib and controls. As shown in FIG. 3A, in the control group, the patients' average value of 44 cytokines decreased after standard therapy while the other four including macrophage inflammatory protein 1α (MIP-1α), granulocyte colony stimulating factor (G-CSF), interferon-a2 (IFN-a2) and interleukin-1a (IL-1a) increased. In contrast, all average values of 48 cytokines decreased in patients on D3 in ruxolitinib group. Furthermore, the average fold-change in ruxolitinib group was 0.466, while it was 0.739 in the control group. The ratios were significantly lower in ruxolitinib group (P<0.0001). Moreover, the levels of seven cytokines including interleukin-6 (IL-6), nerve growth factor β (NGF-β), interleukin-12 (IL-12) (p40), macrophage migration inhibitory factor (MIF), MIP-1α, macrophage inflammatory protein 1β (MIP-1β) and vascular endothelial growth factor (VEGF) were markedly decreased in the ruxolitinib group but not in the control group (FIG. 3 B-I).

Within these cytokines, IL-12 (p40), MIP-1α, MIP-1β and VEGF act as chemoattractants for monocytes, macrophages and other cells to promote the migration of stimulated cells to the site of inflammation. MIF is a proinflammatory lymphokine involved in innate cell-mediated immunity, immunoregulation and inflammation, which regulates macrophage function in host defense. IL-6 is a multifunctional cytokine produced by various cells and regulates physiological activities of various immune cells. These results clearly suggest that ruxolitinib may exert its effect by targeting immune system cells, such as monocytes and macrophages.

DISCUSSION

The described randomized controlled trial found that ruxolitinib with SoC treatment was well tolerated with low to non-hematological toxicities. The demographic and clinical characteristic of the patients, including demographic characteristics, baseline laboratory test result, distribution of ordinal scale scores/National Early Warning Score 2 (NEWS2) scores, were comparable between two enrolled groups at enrollment. All ruxolitinib recipients were able to complete the full course of administration until discharge. While the control group needed much more intensive supportive treatments after enrollment due to the deterioration occurred in some cases, the use of corticosteroid as well as antivirals were well balanced between the control and ruxolitinib group. Addition of ruxolitinib based on SoC did not increase the risk of adverse events in comparison to the control group. The overall incidences of hematological, non-hematological adverse events or chemical laboratory abnormalities were similar between the two arms. Interestingly, while most of the adverse events occurred at grade 1-2, adverse events at grade 3-4 were more common in control group due to the progressive deterioration of COVID-19 in the control arm. Of all ruxolitinib recipients, only two adverse events at grade 3-4 occurred including one with lymphocytopenia and another with hypertension, both of which were transient and reversible. No unexpected adverse events that were previously unknown occurred in ruxolitinib recipients. One of the major concerns with regard to the use of ruxolitinib in the treatment of COVID-19 was its therapeutic action to reduce systemic inflammation, which could potentially unfavorably delay the clearance of viral loads or, even worse, facilitate the spread of virus and impair the host's ability to generate SARS-CoV-2-specific antibodies. In the current study, Applicant did not find a significant difference in viral RNA loads or duration in ruxolitinib recipients as compared with the control group. Interestingly, the mean peak level of IgM specific for SARS-CoV-2 was profoundly higher in the ruxolitinib group than that in the control group, while no significant difference was found in the mean peak of IgG against SARS-CoV-2 between the two groups. The favorable side-effect profile observed in the current trial strongly support the rationale to initiate a large scale multicenter clinical trial at the same or higher ruxolitinib dose regimens in an effort to improve outcomes.

This study found addition of ruxolitinib based on SoC significantly mitigated exuberant cytokine storm featured in severe COVID-19, which justified the use of ruxolitinib to reduce systemic inflammation. In two recent published autopsy reports[31,32], severe immune injury was observed in other organs without obvious viral inclusions, indicating the important role of cytokine storm direct damage of organs in the body by the virus itself. The infiltrated immune cells in alveoli were majorly macrophages and monocytes which is in accordance with Applicant's findings of cytokines changes. In particular, the levels of seven cytokines including IL-6, NGF-β, IL-12(p40), MIF, MIP-1α, MIP-1β and VEGF were markedly decreased in patients received ruxolitinib but not in control group. Among these cytokines, IL-6 had been reported to be a key cytokine driving proinflammatory activity in cytokine-mediated organ dysfunction and tissue damage[33] and IL6-directed therapy is the cornerstone of cytokine-based therapy after CAR-T cell therapy[34,35]. IL-12 (p40), MIP-1α and MIP-1β are critical cytokine/chemokines not only to recruit activated monocytes/macrophages and other cells to the site of infection but also the release of immune cells from the bone marrow or spleen typically featured in coronavirus infection[36-38]. VEGF has been reported to not only recruit monocytes/macrophages but also played a role in increased capillary permeability syndrome that characterizes some type of viral pneumonia[39]. These results indicated that ruxolitinib may exert its inhibitory effect by targeting multiple critical cytokines rather than any specific cytokine, and these cytokines/chemokines could also be employed as surrogate biomarkers in future ruxolitinib trials. Thus, ruxolitinib treatment downregulated a few cytokines and chemokines. These cytokines/chemokine may serve as biomarkers for early identification of severe patients in addition to clinical criteria for severe patients. Further, these identified biomarkers could also be employed as biomarkers for therapeutic response in to ruxolitinib treatment.

For efficacy of ruxolitinib treatment, patients treated with ruxolitinib had a trend of faster clinical improvement as compared with those in the control group (12 [IQR 10-19] days versus 15 [IQR10-18] days, log-rank test P=0.15). Consistent with the findings, ruxolitinib recipients showed faster improvement in the chest CT within 14 days than control group (18 (90%) versus 13 (61.9%), P=0.07). The clinical improvement as defined by Seven-category scale was numerical higher at $D_7$, $D_{14}$ in ruxolitinib recipients than in control group with no statistics significance. Interestingly, patients treated with ruxolitinib showed a significantly shorter lymphocyte recovery than those in the control group (5 [IQR 2-7] days versus 8 [IQR 2-11] days, P=0.03). Applicant therefore proposes that a faster recovery from lymphopenia is of clinical relevance since lymphopenia was associated with poor prognosis. A shorter duration of lymphopenia in ruxolitinib recipients was consistent with a higher mean peak level of IgM specific for SARS-CoV-2 peak IgM in patients treated with ruxolitinib. Also, Applicant proposes that this characteristic of ruxolitinib was much more favorable in comparison to a steroid which has a profound inhibitory effect on lymphocytes. Strikingly, 4 patients experienced clinical deterioration, and all occurred in control group, of which 3 patients were transferred to the ICU and required intubation and mechanical ventilation. Three patients in control group eventually died of respiratory failure. The 28-day mortality was 14.3% in the comparison group. No death or deterioration occurred in ruxolitinib recipients. These data were very encouraging and hypothesis-generating and justify further trials to determine whether treatment of ruxolitinib can reduce the overall incidences of deterioration and death by effectively reducing systemic inflammation before it becomes out of control.

In sum, this study is the first report of using ruxolitinib to treat severe COVID-19, and the first report of using a pan JAK inhibitor in humans to treat coronavirus pneumonia based on a novel therapeutic rationale. These proof of concept findings are promising and fundamentally important to the global medical community.

Example 1 References

1. Li Q, Guan X, Wu P, et al. Early Transmission Dynamics in Wuhan, China, of Novel Coronavirus-Infected Pneumonia. *N Engl J Med* 2020; 382(13): 1199-207.
2. Zhu N, Zhang D, Wang W, et al. A Novel Coronavirus from Patients with Pneumonia in China, 2019. *N Engl J Med* 2020; 382(8): 727-33.
3. Mahase E. Covid-19: WHO declares pandemic because of "alarming levels" of spread, severity, and inaction. *BMJ* 2020; 368: m1036.
4. Huang C, Wang Y, Li X, et al. Clinical features of patients infected with 2019 novel coronavirus in Wuhan, China. *Lancet* 2020; 395(10223): 497-506.
5. Lai C C, Liu Y H, Wang C Y, et al. Asymptomatic carrier state, acute respiratory disease, and pneumonia due to severe acute respiratory syndrome coronavirus 2 (SARS-CoV-2): Facts and myths. *J Microbiol Immunol Infect* 2020.
6. Guan W J, Ni Z Y, Hu Y, et al. Clinical Characteristics of Coronavirus Disease 2019 in China. *N Engl J Med* 2020.
7. Wang Y, Liu Y, Liu L, Wang X, Luo N, Ling L. Clinical outcome of 55 asymptomatic cases at the time of hospital admission infected with SARS-Coronavirus-2 in Shenzhen, China. *J Infect Dis* 2020.
8. Wang D, Hu B, Hu C, et al. Clinical Characteristics of 138 Hospitalized Patients With 2019 Novel Coronavirus-Infected Pneumonia in Wuhan, China. *JAMA* 2020.
9. Du Y, Tu L, Zhu P, et al. Clinical Features of 85 Fatal Cases of COVID-19 from Wuhan: A Retrospective Observational Study. *Am J Respir Crit Care Med* 2020.
10. Chen N, Zhou M, Dong X, et al. Epidemiological and clinical characteristics of 99 cases of 2019 novel coronavirus pneumonia in Wuhan, China: a descriptive study. *Lancet* 2020; 395(10223): 507-13.
11. Cao Y, Liu X, Xiong L, Cai K. Imaging and Clinical Features of Patients With 2019 Novel Coronavirus SARS-CoV-2: A systematic review and meta-analysis. *J Med Virol* 2020.
12. Cao B, Wang Y, Wen D, et al. A Trial of Lopinavir-Ritonavir in Adults Hospitalized with Severe Covid-19. *N Engl J Med* 2020.
13. Kupferschmidt K, Cohen J. Race to find COVID-19 treatments accelerates. *Science* 2020; 367(6485): 1412-3.
14. Chien J Y, Hsueh P R, Cheng W C, Yu C J, Yang P C. Temporal changes in cytokine/chemokine profiles and pulmonary involvement in severe acute respiratory syndrome. Respirology 2006; 11(6): 715-22.
15. Wang C H, Liu C Y, Wan Y L, et al. Persistence of lung inflammation and lung cytokines with high-resolution CT abnormalities during recovery from SARS. *Respir Res* 2005; 6: 42.
16. Wong C K, Lam C W, Wu A K, et al. Plasma inflammatory cytokines and chemokines in severe acute respiratory syndrome. *Clin Exp Immunol* 2004; 136(1): 95-103.

17. Zhang Y, Li J, Zhan Y, et al. Analysis of serum cytokines in patients with severe acute respiratory syndrome. *Infect Immun* 2004; 72(8): 4410-5.
18. Zhang C, Wu Z, Li J W, Zhao H, Wang G Q. The cytokine release syndrome (CRS) of severe COVID-19 and Interleukin-6 receptor (IL-6R) antagonist Tocilizumab may be the key to reduce the mortality. *Int J Antimicrob Agents* 2020: 105954.
19. Channappanavar R, Perlman S. Pathogenic human coronavirus infections: causes and consequences of cytokine storm and immunopathology. *Semin Immunopathol* 2017; 39(5): 529-39.
20. Peiris J S, Chu C M, Cheng V C, et al. Clinical progression and viral load in a community outbreak of coronavirus-associated SARS pneumonia: a prospective study. *Lancet* 2003; 361(9371): 1767-72.
21. Stebbing J, Phelan A, Griffin I, et al. COVID-19: combining antiviral and anti-inflammatory treatments. *Lancet* Infect Dis 2020.
22. Gu J, Gong E, Zhang B, et al. Multiple organ infection and the pathogenesis of SARS. *J Exp Med* 2005; 202(3): 415-24.
23. Ajayi S, Becker H, Reinhardt H, et al. Ruxolitinib. *Recent Results Cancer Res* 2018; 212: 119-32.
24. Meng G, Wang J, Wang X, Wang Y, Wang Z. Ruxolitinib treatment for SR-aGVHD in patients with EBV-HLH undergoing allo-HSCT. *Ann Hematol* 2020; 99(2): 343-9.
25. Przepiorka D, Luo L, Subramaniam S, et al. FDA Approval Summary: Ruxolitinib for Treatment of Steroid-Refractory Acute Graft-Versus-Host Disease. *Oncologist* 2019.
26. Ahmed A, Merrill S A, Alsawah F, et al. Ruxolitinib in adult patients with secondary haemophagocytic lymphohistiocytosis: an open-label, single-centre, pilot trial. *Lancet Haematol* 2019; 6(12): e630-e7.
27. Trantham T, Auten J, Muluneh B, Van Deventer H. Ruxolitinib for the treatment of lymphoma-associated hemophagocytic lymphohistiocytosis: A cautionary tale. *J Oncol Pharm Pract* 2019: 1078155219878774.
28. China National Health Commission. Diagnosis and treatment of pneumonitis caused by new coronavirus (trial version 5). Beijing: China National Health Commission, http://www.nhc.gov.cn/yzygj/s7653p/202002/3b09b894ac9b4204a79db5b8912d4440.shtml. 2020.
29. Yan Xianghu B Y, Zhu Tong, Ai Tao, Tang Dazhong. COVID-19 pneumonia: C T imaging evolution characteristics of thoracic lesions in recovery stage. *radiologic practice* 2020; 35: 407-10.
30. Coronavirus disease (COVID-2019) R&D. Geneva: World Health Organization http://www.who.int/blueprint/priority-diseases/key-action/novel-coronavirus/en/.
31. Xu Z, Shi L, Wang Y, et al. Pathological findings of COVID-19 associated with acute respiratory distress syndrome. *Lancet Respir Med* 2020.
32. Yao X H, Li T Y, He Z C, et al. [A pathological report of three COVID-19 cases by minimally invasive autopsies]. *Zhonghua Bing Li Xue Za Zhi* 2020; 49(0): E009.
33. Crayne C B, Albeituni S, Nichols K E, Cron R Q. The Immunology of Macrophage Activation Syndrome. *Front Immunol* 2019; 10: 119.
34. Kotch C, Barrett D, Teachey D T. Tocilizumab for the treatment of chimeric antigen receptor T cell-induced cytokine release syndrome. *Expert Rev Clin Immunol* 2019; 15(8): 813-22.
35. Chen H, Wang F, Zhang P, et al. Management of cytokine release syndrome related to CAR-T cell therapy. *Front Med* 2019; 13(5): 610-7.
36. Schulz O, Hammerschmidt S I, Moschovakis G L, Forster R. Chemokines and Chemokine Receptors in Lymphoid Tissue Dynamics. *Annu Rev Immunol* 2016; 34: 203-42.
37. Cooper A M, Khader S A. IL-12p40: an inherently agonistic cytokine. *Trends Immunol* 2007; 28(1): 33-8.
38. Menten P, Wuyts A, Van Damme J. Macrophage inflammatory protein-1. *Cytokine Growth Factor Rev* 2002; 13(6): 455-81.
39. Olsson A K, Dimberg A, Kreuger J, Claesson-Welsh L. VEGF receptor signalling—in control of vascular function. *Nat Rev Mol Cell Biol* 2006; 7(5): 359-71.

Example 2—Clinical Trial Entitled "2019-nCoV Severe Pneumonia Patients Treated with Ruxolitinib: A Prospective, Multi-Center, Single Blind, Randomized Controlled Clinical Trial"

I. Background

A novel coronavirus (2019-nCoV) was discovered at the end of 2019 because of an atypical viral pneumonia in Wuhan, and it was named by the World Health Organization on Jan. 12, 2020. According to the "information of the first strain of 2019-nCoV" released by the National Institute for Viral Disease Control Prevention, Chinese Center for Disease Control and Prevention, the virus is similar with the 2003 Severe Acute Respiratory Syndrome (SARS) coronavirus and the Middle East Respiratory Syndrome (MERS) coronavirus, which all belong to β coronavirus, and its sequence has 80% and 40% homology with the two, respectively. The virus is a single-stranded RNA virus with a full-length genome of 29.8 kb and can mutate rapidly and integrate. The virus is likely to be closely related to the coronavirus carried by Chinese horseshoe bats [1]. As of 0:00 Jan. 29, 2019, there were 5,974 confirmed cases, including 1,239 severe cases and 132 deaths. To date, the infection is still prevalent, involving many countries and regions around the world. The number of affected people in the prevention, control, and treatment of infection has reached billions. Thus, it is currently the most urgent medical emergency to be solved.

As published in Lancet, most of the infected patients this time were young adults and healthy ones, with a median age of 49 years (IQR 41-58 years), and 32% of patients had underlying diseases. For the confirmed cases, 98% had fever, 76% had cough, 44% had myalgia or fatigue, 55% had dyspnea, and 63% had lymphopenia. All patients admitted had pneumonia with ground-glass lesions of viral pneumonia on chest CT. In addition, atypical symptoms included: sputum production (28%), headache (8%), haemoptysis (5%), and diarrhea (3%). Complications included acute respiratory distress syndrome (29%), acute cardiac injury (12%), and secondary infections (10%) [2].

At present, 32% of the 2019-nCoV patients need to be admitted to the Intensive Care Unit (ICU) for treatment, and the mortality of admitted patients reaches 15%, while 68% of patients only need symptomatic supportive treatment, and their conditions can be quickly improved. There have been some patients receiving early treatment with results of two swab tests of virus being negative, reaching the discharge standards, and they have been cured and discharged. However, some severe cases have died of lung failure, acute respiratory distress syndrome and hypovolemic shock. With the prolonged disease course (more than 3 weeks), some have developed fibrosis in the lung tissues, resulting in impaired lung function and long-term disability. For 2019- nCoV pneumonia, there are currently many key scientific issues that need to be solved. It is crucial to solve the following problems to effectively prevent and control the overall mortality of pneumonia, reduce the disability rate, and eliminate the social panic. These problems include: 1. The current clinical treatment can only identify mild or severe cases according to clinical features and progression, without any predictability. Biomarkers determining the conditions are urgently needed for early stratification and treatment; 2. The mechanism of severe pneumonia caused by the virus is poorly understood, and there are only symptomatic and life support treatments, but the efficacy is not significant. After identifying some mechanisms, the rate of successful rescue is expected to be increased significantly; 3. At present, only symptomatic treatment is available for 2019-nCoV pneumonia. The development of antiviral drugs and vaccines is still ongoing, which cannot meet emergencies. Thus, it is imperative to seek clinically effective therapies available now for treatment of other diseases, which can reduce the mortality and long-term disability rate.

The current theoretical and research advances of infectious diseases, Chimeric Antigen Receptor (CAR)-T cell therapy-related cytokine release syndrome, and primary and secondary hemophagocytic syndromes provide a good theoretical basis for Applicant's research, and reasonable and realistic possibilities to solve the above-mentioned key clinical problems, The pathogenesis of 2019-nCoV pneumonia may be due to the uncontrolled inflammation caused by cytokine release: Cytokine release syndrome (CRS), also known as cytokine storm, is a systemic and non-antigen-specific toxic response caused by high activation of immune cells and excessive release of cytokines, resulting from inducements of a variety of infections, rheumatic immune diseases or tumors. It is mainly characterized by hyperthermia, hypotension, hypoxemia, and multiple organ toxicity and/or failure.

Some known severe viral infections, such as EBV infection, can lead to fatal cytokine storm, also known as hemophagocytic lymphohistiocytosis. For coronaviruses, regardless of SARS or MERS-CoV infection, there will be dramatic up-regulation of pro-inflammatory cytokines and cytokine storm. These cytokines include IFNγ, TNFα, IL15, IL1B, etc. [5,6]. An excessive cytokine storm not only damages the organs infected by the virus, but even in the organs that are not involved by the infected pathogen, the cytokines themselves can cause severe damage.

In the recently published articles studying 2019-nCoV, researchers conducted a lineage study of 27 cytokines and chemokines, and these included: IL1B, IL1RA, IL2, IL4, IL5, IL6, IL7, IL8 (also known as CXCL8), IL9, IL10, IL12p70, IL13, IL15, IL17A, Eotaxin (also known as CCL11), basic FGF2, GCSF (CSF3), GMCSF (CSF2), IFNγ, IP10 (CXCL10), MCP1 (CCL2), MIP1A (CCL3), MIP1B (CCL4), PDGFB, RANTES (CCL5), TNFα, and VEGFA. The results showed that compared with healthy people, the concentrations of IL1B, IL1RA, IL7, IL8, IL9, IL10, basic FGF, GCSF, GMCSF, IFNγ, IP10, MCP1, MIP1A, MIP1B, PDGF, TNFα and VEGF in the plasma among 2019-nCoV infected patients (regardless of critically ill patients admitted to ICU and mild ones not admitted to ICU) were significantly increased. Among them, the up-regulation of cytokines, such as IL1B, IFNγ, IP10, and MCP1 in 2019-nCoV infected patients may be related to the response of activated Th1 cells. The cytokines IL4 and IL10 secreted by Th2 cells were also up regulated. These results indicated that a typical cytokine storm was present in patients with 2019-nCoV pneumonia. Notably, IL2, IL7, IL10, GCSF, IP10, MCP1, MIP1A, and TNFα levels are significantly higher in critically ill patients admitted to ICU than in non-ICU mild ones, suggesting that cytokine storm is associated with the severity of 2019-nCoV infection [2].

The treatment of cytokine storm can successfully reverse multiple fatal inflammatory diseases: CRS is a main complication in CAR-T cell immunotherapy. During CAR-T cell immunotherapy, corticosteroid and IL6 antagonist Tocilizumab are used for treatment of CRS [3,4], which has achieved good results, successfully reversing the fatal cytokine storm. In hemophagocytic lymphohistiocytosis caused by multiple factors, etoposide in combination with dexamethasone to suppress cytokine storm can successfully reverse severe multiple organ failure. In the acute rejection of hematopoietic stem cell transplantation, immunosuppressive therapy can successfully reverse severe transplantation rejection, contributing to long-term survival of the patients. The mechanism is to directly adopt immunosuppression or regulation to timely block the uncontrolled cytokine storm and provide the most important intervention opportunity for the patient to get through the critical stage.

Feasible treatment options for cytokine storm: Current treatment options on cytokine storm in clinics include chemotherapeutic drugs (e.g. etoposide), immunosuppressants (e.g. glucocorticoids, cyclosporine, etc.), cytokine monoclonal antibodies (e.g. anti-IL6 cytokine receptors, anti-TNFalpha, anti-INFgamma antibodies, etc.), small molecule compounds (e.g. rucotinib), cell preparations (e.g. mesenchymal stem cell preparations), plasma replacement, and so on. The appropriate treatment options should be determined by analyzing critical pathophysiological mechanisms of different diseases.

Ruxolitinib is a selective tyrosine kinase inhibitor that selectively inhibits JAK1/JAK2 kinase, and was first approved by FDA for the treatment of primary myelofibrosis (PMF) and other myeloproliferative diseases [7]. Persistent activation of inflammatory factors in PMF plays an important role in the occurrence, transformation and maintenance of this malignant disease. A series of studies have found that multiple cytokines, including IL-8, IL-2R, IL-12, and IL-15, were elevated in patients with myelofibrosis, indicating prognostic significance [8-9]. During ruxolitinib treatment on myelofibrosis, the reduction in cytokine levels is often accompanied by a decrease in disease burden [10].

Recently, ruxolitinib has been found to inhibit the secretion of inflammatory factors by T cells, increase the number of regulatory T cells, and reduce T cell surface-related chemokines or chemokine receptors, thereby altering T cell migration. Therefore, it has obvious therapeutic effects on inhibiting T cell overactivation, controlling uncontrolled inflammatory response and hemophagocytic syndrome. The related phenomena have been observed in various animal models and clinical trials [11-14]. It has been used to control cytokine storm in hematopoietic stem cell transplantation with graft-versus host disease (GVHD) (essentially the overactivation of T lymphocytes) and cellular immunotherapy [15]. Above all, ruxolitinib has shown good efficacy in controlling a series of diseases caused by proinflammatory factor activation, including cytokine overactivation and fibrotic diseases.

For the most critical features of out-of-control immunity, a prospective, single-blind, randomized controlled clinical study of ruxolitinib in the treatment of 2019-nCoV severe pneumonia patients is conducted to explore the practical clinical solutions for severe and critical cases, and further, a cohort of 2019-nCoV pneumonia is established to observe the long-term health and quality of life of these patients.

II. Research Purpose

Primary purpose: The study is designed to test the safety and efficacy of this this novel treatment strategy.

Secondary purpose: 1) The recovery rate as assessed with the seven-category ordinal scale on D7, D14, D21 and D28, follow-up CT scans within two weeks, the duration of randomization to lymphocyte recovery and to mechanical ventilation, the duration of hospitalization in survivors, and the time (in days) from treatment initiation to death and virus clearance time 2) the study is designed to study the overall mortality at D28.

Investigational purpose: the study is designed to detect the dynamic changes of the virus copies, cytokines, 2019 nCoV-specific antibody and its correlation with clinical treatment response.

III. Research Objectives

Through a prospective controlled clinical study, it is hoped to evaluate the safety and effectiveness of the new treatment regimen, to achieve the goal of rapidly alleviating clinical symptoms of severe coronavirus pneumonia patients, reduce mortality rate, improve quality of life of severe pneumonia patients, and reduce occurrence of pulmonary fibrosis, providing a new treatment approach.

A cohort study of 2019-nCoV pneumonia based on prospective new studies is established to follow up the long-term health status and quality of life of these patients.

IV. Research Protocol

Study design. In this study, a prospective multi-center randomized controlled trial (RCT) is used to evaluate the improvement rate and cure rate of ruxolitinib in the treatment of severe 2019-nCoV pneumonia. Randomized grouping scheme: After signing informed consent form, patients were then randomly allocated into two groups with a 1:1 allocation ratio by an independent statistician using permuted blocks of 4 for all sites. Patient unique identification number and treatment allocation codes were provided in sequentially numbered opaque envelops.

Study Endpoints

Primary outcomes. The primary safety endpoint was the incidence of serious adverse events occurring up to 28 days. The primary efficacy end point was the time to clinical improvement, defined as the time from randomization (D0) to an improvement of two points on a seven-category ordinal scale or live discharge from the hospital (Dend). Other clinical outcomes included status as assessed with the seven-category ordinal scale on D7, D14, D21 and D28, follow-up CT scans within two weeks etc.

Secondary outcomes. The secondary endpoint is the overall mortality at D28.

Study Population

Inclusion Criteria

1. Aged ≥18 years and ≥75 years;
2. Patients clinically diagnosed as novel coronavirus infection; or with positive serum antibodies (IgM or IgG); or with novel coronavirus infection confirmed by PCR;
3. Severe/critical patients.

Exclusion criteria: Patients with other malignant tumors requiring treatment; Severe cardiovascular and metabolic diseases beyond the control of combination with other drugs; Patients with clinical symptoms of brain dysfunction or serious mental illness who cannot understand or follow the study protocol; Endotracheal intubation with invasive ventilation; Patients who cannot guarantee completion of necessary treatment plan and follow-up observation; Women of child-bearing age who are positive in pregnancy test or do not stop breastfeeding in lactation period; Patients with other infections at the time of enrollment; Other circumstances that prevent the protocol from proceeding safely.

Criteria for rejection and dropout: During treatment and follow-up period, due to changes in disease or death unrelated to experimental factors occur, patients cannot continue to be observed.

Termination criteria: Patients with severe adverse reactions that cannot be tolerated; Patients voluntarily ask to quit the clinical trial; Pregnancy; Patients having severe infection with other clearly identified pathogens; At least 3 days after administration, ANC and PLT reduce by >50% from baseline; Patients unsuitable for further treatment due to other reasons considered by investigators.

Treatment Plans

Medicines and Cells

Medicine: Ruxolitinib; Manufacture: Novartis PharmaSteinAG; Strength: 5 mg/Tablet; Standards for Registration of Imported Drugs: JX20140057; Approval No.: H20170134; Storage: ambient temperature. Administration: oral, with or without food, 5 mg twice a day.

Experimental Group (Ruxolitinib Plus Standard-of-Care)

Patient enrollment: according to the Hubei Provincial Standards of 'Diagnosis and Treatment Scheme for Pneumonia Infected by Novel Coronavirus (Trial Edition 5)', all patients with severe novel coronavirus pneumonia were given the current general treatment (including corticosteroid judged by doctors);

Treatment: Investigators judge whether patients are eligible for enrollment. After obtaining patients' consent, the patients start oral administration of ruxolitinib 5 mg twice a day, every 12 h until complete clinical remission or disease progression.

Figure 4:
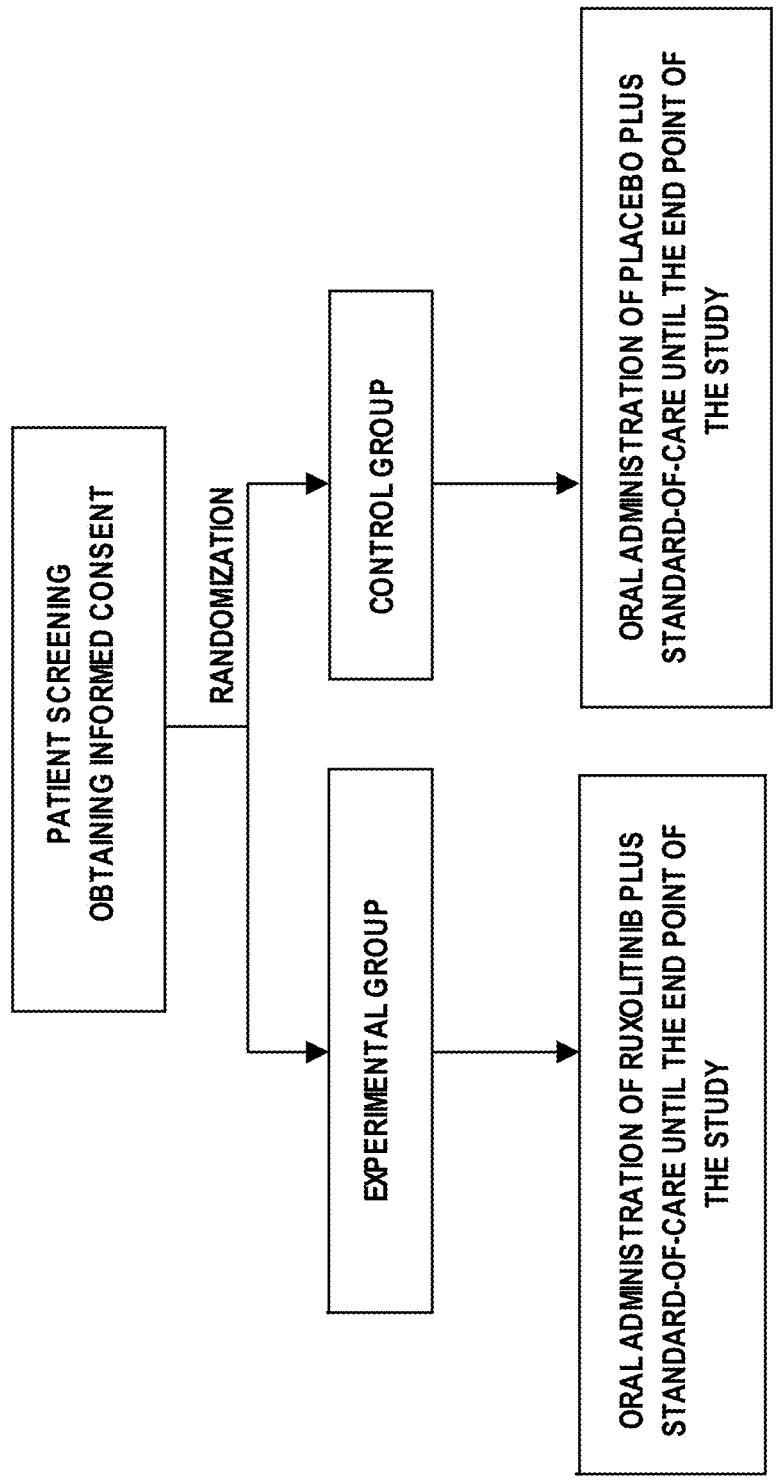
FIG. 4. Flow chart showing patient enrollment scheme for trial described in Example II.

The specific flow chart is shown in FIG. 4.

During the course of treatment, overall response rate, fastest response time, duration of efficacy, and mortality of 2019-nCoV severe pneumonia patients are followed up and observed. The main monitoring indices include clinical scores, imaging indices and virological detection evidence. Lung function, disability rate and quality of life are dynamically observed during follow-up.

Randomization

Control Group (Placebo Plus Standard-of-Care)

Patients enrollment: according to the Hubei Provincial Standards of 'Diagnosis and Treatment Scheme for Pneumonia Infected by Novel Coronavirus (Trial Edition 5)', all patients with severe novel coronavirus pneumonia are given the current general treatment. Overall response rate, fastest response time, duration of efficacy, and mortality of severe novel coronavirus pneumonia patients are followed up and observed. The main monitoring indices include clinical scores, imaging indices and virological detection evidence. Lung function, disability rate and quality of life are dynamically observed during follow-up.

Clinical diagnosis and classification criteria: Diagnosis and treatment scheme of 2019-nCoV pneumonia (5th trial edition) Hubei Province Standard.

Diagnostic Criteria (Hubei Province):

1. Suspected cases.

Comprehensive analysis based on the following epidemiological history and clinical features:

1) Epidemiological history (1) Travelling or living history of Wuhan and its surrounding areas or other communities with case reports within 14 days before the onset of illness (2) Exposure to people from Wuhan and its surrounding areas, or patients with fever or respiratory symptoms in communities with case reports within 14 days before the onset of illness;

(3) Clustered onset;

(4) History of exposure to patients infected with 2019-nCoV, who were those with positive result of nucleic acid test 2) Clinical features (1) fever and/or respiratory symptoms;

(2) The total white cell count was normal or decreased, or the lymphocyte count was decreased in the early stage of disease.

(3) Having any of the epidemiological history or no epidemiological history, and meeting 2 of the clinical features at the same time.

Clinically Diagnosed Cases

Suspected cases with imaging features of pneumonia.

Confirmed Cases

Clinically diagnosed or suspected cases with one of the following etiological evidence:

1) Real-time fluorescent RT-PCR of respiratory or blood specimens showed positive result of nucleic acid test for 2019-nCoV;

2) Result of gene sequencing of virus in respiratory or blood specimens was highly homologous to known 2019-nCoV.

Clinical Classification:

(1) Mild.

The clinical symptoms were mild, and there were no imaging features of pneumonia.

(2) General.

There was fever, respiratory symptoms, as well as imaging features of pneumonia.

(3) Severe.

Meeting any of the following items:

1. Respiratory distress, RR≥30 breaths/min;

2. In the resting state, the oxygen saturation ≤93%;

3. Partial pressure of oxygen in arterial blood (PaO2)/fraction of inspired oxygen (FiO2)≤300 mmHg (1 mmHg=0.133 kPa).

(4) Critically ill.

Meeting any of the following items:

1. Respiratory failure needing mechanical ventilation;

2. Shock;

3. Being complicated with other organ failures needing ICU monitoring and treatment.

Enrollment and Examination Plan

Once patients are enrolled, the collected information includes:

Demographic data. The following information should be obtained and recorded from the subjects or relevant personnel: (age, sex, race and race)

Baseline Evaluation

Current medical history: current symptoms include fever, sore throat, cough, fatigue, weakness, dizziness, blurred consciousness, headache, myalgia, vomiting, diarrhea, symptoms, abdominal pain, chest pain, dyspnea, etc.

Previous history: underlying respiratory diseases, cardiovascular system, metabolic system, etc.

Baseline clinical data: vital signs, blood pressure, oxygen saturation; weight/height; clinical indices related to pneumonia classification, imaging manifestations. Baseline laboratory examinations: blood routine, blood biochemistry, coagulation function, cytokines, CRP, PCT, chest CT, EKG, blood gas analysis; throat swab for nucleic acid detection.

Observation of Therapeutic Effect

The changes of clinical scores and symptoms are recorded daily after enrollment.

After D7 of ruxolitinib administration, clinical scores are evaluated to determine the therapeutic response of the disease and determine whether MSCs are injected or not.

Record adverse events daily;

Record the combined medication;

Chest CT imaging features before and after treatment;

Observation on the key immunoassay indices before and after treatment: after the informed consent is signed by the patients diagnosed with 2019-ncov pneumonia, peripheral blood and urine samples are collected on D1 for treatment and properly preserved for testing. The second test point is DX, the next day after the change of disease. The so-called disease change refers to the improvement or deterioration of the treatment response (grade upgrade, clinical score increase or imaging progress) based on the conventional treatment. The third test point is the day before the patient discharged after reaching the clinical cure standard Dend. In addition to routine testing, clinical subjects need to reserve sufficient peripheral blood samples for exploratory studies of 48 cytokines, ferritin and 2019-nCoV virus copies, as well as urine samples (intended for metabolomic studies).

Monitoring and Follow-Up

Patient completes the monitoring plan listed in Section 6 during hospitalization, except for those who quit the trial. The investigators will decide whether the patient is suitable for discharge according to the results of the examination and recovery of the adverse reactions. After discharge, patients need to be followed up as follows:

Short-Term Follow-Up Period

Within 3 months after completion of the treatment, patient will be admitted to the hospital for a follow-up once a month to follow up and evaluate the short-term safety and effectiveness of the treatment. Medium and long-term follow-up period Within 12 months after completion of the short-term follow-up, patient will be admitted to the hospital for follow-up every 2 months to follow up and evaluate the safety and effectiveness of the treatment in medium and long term.

The medication plan, clinical evaluation, and laboratory monitoring are listed during follow-up.

Flow chart of treatment and follow-up. *Optional examination items; #Experimental group

| Visiting No.<br>Visiting time window | Screening stage<br>Visiting 1<br>D-7-D0 | Ruxolitinib treatment#<br>Visiting 2<br>D1-7<br>Evaluation on the clinical or radiological effects | Visiting 3<br>Stable or progress evaluated by efficacy<br>D8 D11 D14 | Hospital follow-up period<br>Visiting 4 (daily)<br>D1-D30 | Short-term follow-up observation period<br>Visiting 5 (monthly)<br>D60 D90 | Medium/long-term follow-up observation period<br>Visiting 6 (every two months)<br>D150 D210 D270 D330 D390 ± 7 | Follow-up quitting<br>Visiting 7<br>Anytime |
|---|---|---|---|---|---|---|---|
| Informed consent | ✓ | | | | | | |
| Evaluation of inclusion/exclusion criteria | ✓ | | | | | | |
| Demographic information | ✓ | | | | | | |
| Previous Medical history | ✓ | | | | | | |
| Previous treatment history | ✓ | | | | | | |
| Vital signs examination[1] | ✓ | ✓ | ✓ | ✓ | ✓ | ✓ | ✓ |
| Physical examination[2] | ✓ | ✓ | ✓ | ✓ | ✓ | ✓ | ✓ |
| Blood pregnancy test | ✓ | | | | | | ✓ |
| Blood routine examination[3] | ✓ | ✓ | ✓ | ✓ | ✓ | ✓ | ✓ |
| Blood biochemistry[4] | ✓ | ✓ | ✓ | ✓ | ✓ | ✓ | ✓ |
| Coagulation function | ✓ | ✓ | ✓ | ✓ | ✓ | ✓ | ✓ |
| Blood Gas Analysis | ✓* | | | | | | |
| Electrocardiogram | ✓ | ✓ | ✓ | ✓ | ✓ | ✓ | ✓ |
| Procalcitonin | ✓ | ✓ | ✓ | ✓ | ✓ | ✓ | ✓ |
| C-reaction protein | ✓ | ✓ | ✓ | ✓ | ✓ | ✓ | ✓ |
| HBV, HCV, HIV[5] | ✓ | | | | | | |
| Detection of virus nucleic acid[6] | ✓ | | | ✓ | ✓ | ✓ | ✓ |
| Lung function examination[7] | | | | ✓* | ✓ | ✓ | ✓ |
| Cardiac evaluation[8] | ✓* | | | | | | |
| Chest CT | ✓ | | | ✓ | ✓ | ✓ | ✓ |
| Cytokine detection[9] | ✓ | ✓ | ✓ | ✓ | ✓ | ✓ | ✓ |
| Ferritin[10] | ✓ | ✓ | ✓ | ✓ | ✓ | ✓ | ✓ |
| Oral ruxolitinib | | ✓ | ✓ | | | | |
| Combined treatment record[11] | ✓ | ✓ | ✓ | ✓ | ✓ | ✓ | ✓ |
| Prohibited drug record[12] | ✓ | ✓ | ✓ | ✓ | ✓ | ✓ | ✓ |
| Adverse event record | ✓ | ✓ | ✓ | ✓ | ✓ | ✓ | ✓ |

Experimental Group

Note: Examination of vital signs: it should include at least blood pressure, heart rate, respiratory rate, blood oxygen saturation (oxygen inhalation and deoxygenation for 10 minutes) and temperature examination. During visits 2-4, patients should measure and record the axillary temperature and blood pressure (diastolic blood pressure and systolic blood pressure) twice a day (8:00 and 20:00, respectively);

Physical examination: including general conditions, physical strength, bleeding, jaundice, etc.

Blood routine examination: In addition to the visit time points in the flowchart, the examination should be performed at least once a week during visit periods of treatment and hospital stay according to clinical needs.

Blood biochemistry: it should at least include serum lactate dehydrogenase (LDH), total bilirubin, indirect bilirubin, direct bilirubin, creatinine, alanine aminotransferase, aspartate aminotransferase, cholesterol, electrolytes, blood glucose and albumin to evaluate the liver and renal function of patients. It should be performed at least once a week during visit periods of treatment and hospital stay.

HBV, HCV and HIV test: Patients completed the test 3 months before enrollment and the results were valid, and needed not to undergo the test;

Viral nucleic acid test: Standard test reagents were used. The type of test specimen was not limited to throat swabs and sputum;

Pulmonary function test: At least it should include forced expiratory volume in 1 second (FEV1), forced vital capacity (FVC) and diffusing capacity of the lung for carbon monoxide (DLCO). Based on the patient's previous treatment history, the patient's lung function should be fully assessed.

Because the 2019-nCoV was highly infectious, no requirements were made during the screening, treatment, and hospitalization, and follow-up periods unless the patient met the criterion of cure.

Cardiac evaluation: The patient's cardiac function can be assessed based on the patient's previous treatment history, including cardiac color ultrasound, electrocardiogram, troponin, NT-pro-BNP, etc.; reexamination can be performed at any time according to the conditions;

Cytokine detection: It is used to monitor the severity of cytokine storm, including but not limited to IL-6, IL-10, IFN-$\gamma$, TNF-$\alpha$ and other cytokines. During the treatment of ruxolitinib, at least once every three days is required. Except for the time point of visit in the flow chart, the number of detection can be increased according to the needs of the disease. The detection is conducted in a laboratory package.

Ferritin: used to monitor the activation degree of macrophages. In addition to the time point of visit in the flow chart, if ferritin is significantly increased, it is required to conduct at least once every three days during the treatment of ruxolitinib. The times of detection can be increased according to the condition, until the second consecutive normal or clinical remission of the disease.

C-reaction protein detection: To monitor the severity of cytokine storm and investigate its correlation with cytokines. In addition to the visit time point in the flowchart, it is required that during ruxolitinib treatment, at least once every three days; in addition to the visit time point in the flowchart, the times of tests can be increased according to the needs of the disease until two consecutive normal or clinical remission of the disease.

Combined treatment record: used to record all combined treatments during the trial, including combined medication and supportive treatment in case of adverse reactions;

Prohibited drug record: used to record the use of prohibited drugs during the trial, such as other cytokine antagonists, chemotherapeutic drugs, etc.

During the visit, if cytokine, ferritin and viral nucleic acid tests are performed twice and the results are all below the lowest limit, the corresponding tests in the follow-up visit of the patient can be cancelled.

During treatment, the investigator can conduct necessary examinations other than those prescribed by the patient's disease and adverse reactions, such as (long-range) electrocardiogram, troponin, nuclear magnetic resonance, gastrointestinal endoscopy, etc.

Observation Indices and Efficacy Evaluation Criteria
Observation index: clinic
Clinical indices: 1 point for each
1) Disturbance of consciousness
2) BUN>7 mmol/L
3) respiratory rate≥30 times/min
4) Hypotension (systolic pressure <90 mmHg or diastolic pressure≤60 mmHg)
5) Blood oxygen index, PaO2/FiO2≤300 mmHg
Criterion of cure: 0
Criterion of improvement: decrease by 2 points. If it is 4, it will be 2 after treatment
Criterion of ineffectiveness: 5, or requiring invasive ventilation, or death. The integral increases to progress.
Observation Indicators: Imaging
Imaging standard: 50% improvement in lesion area is cure, 10-20% improvement in lesion area is improvement; no change or increase in lesion area is effective, and area increase is progress.

Evaluation index of virus efficacy: after treatment, pharyngeal swab 2019-ncov virus nucleic acid test turning from positive to negative in two consecutive tests is considered as virological negative.

Clinical cure: the virology turning negative and conforming to the judgment standards of clinical index curative effect and imaging curative effect is clinical cure.

Determination of Statistical Hypothesis and Sample Size
Total Number of Cases

In the view of sample composition, patients are divided into experimental group (ruxolitinib treatment group) and control group (placebo treatment group). The estimation equation of sample size in unilateral test according to the difference of two sample rates is as follows:

$$n_1 = \frac{\left[z_x\sqrt{p(1-p)(1+c)/c} + z_\beta\sqrt{p_1(1-p_1) + p_2(1-p_2)/c}\right]^2}{(p_1 - p_2)^2}$$

Where, c=n1/n2. If the statistically significant difference is set as 0.05, the detection efficacy (power, P) is set as 0.80. 40% difference is assumed in term of CT improvement within 14 days after randomization between the two groups with approximately 50% patients in group A. After the result is substituted into the above equation, the number of cases needed in each group is calculated as 40 and 20 cases are needed in each group. The number of cases in the experimental group and control group is 1:1.

V. Regulations for Technical Operations

This clinical study was carried out in strict accordance with 2019 Guidelines for Biosafety Protection of 2019-nCoV pneumonia in Clinical Laboratory Testing (First Edition) and Technical Guidelines for Laboratory Testing of 2019-nCoV pneumonia (Second Edition);

Severe 2019-nCoV pneumonia should be treated in accordance with "critical medicine, infectious disease treatment/care routine";

The laboratory management shall be conducted in accordance with the "P2, P4 Laboratory Management Regulations".

VI. Measures for Quality Control

Investigators have qualifications and rich clinical experience in intensive care medicine/internal medicine The detailed study protocol should be developed, and a CRF form should be designed to submit to Ethics Committee for consideration.

Quality control personnel should be arranged for clinical study to regularly check the study progress and implement quality control.

VII. Technical Risk and Emergency Disposal Plan

Relevant risk and emergency disposal plan of this study will be implemented according to the relevant rescue plan in the Standard Operating Procedure (SOP) of Clinical Drug Trials for Critical Care Medicine, which mainly includes the following contents:

Standards for disposal of residues of biological products, first-aid plan for anaphylaxis, first-aid plan for shock, first-aid plan for cardiac arrest, first-aid plan for respiratory failure, first-aid plan for acute renal failure, first-aid plan for multiple organ dysfunction syndrome (MODS), first-aid plan for bleeding etc.

Example 2 References

1. Chan J F, Yuan S, Kok K H, To K K, Chu H, Yang J, Xing F, Liu J, Yip C C, Poon R W, Tsoi H W, Lo S K, Chan K H, Poon V K, Chan W M, Ip J D, Cai J P, Cheng V C, Chen H, Hui C K, Yuen K Y. Lancet. 2020 Jan. 24. pii: S0140-6736(20)30154-9. doi: 10.1016/S0140-6736(20)30154-9. [Epub ahead of print]
2. Huang C, Wang Y, Li X, Ren L, Zhao J, Hu Y, Zhang L, Fan G, Xu J, Gu X, Cheng Z, Yu T, Xia J, Wei Y, Wu W, Xie X, Yin W, Li H, Liu M, Xiao Y, Gao H, Guo L, Xie J, Wang G, Jiang R, Gao Z, Jin Q, Wang J, Cao B. Lancet. 2020 Jan. 24. pii: S0140-6736(20)30183-5. doi: 10.1016/S0140-6736(20)30183-5. [Epub ahead of print]
3. Lee D W, Gardner R, Porter D L, Louis C U, Ahmed N, Jensen M, Grupp S A, Mackall C L. Blood. 2014 Jul. 10; 124(2):188-95. doi: 10.1182/blood-2014-05-552729. Epub 2014 May 29. Erratum in: Blood. 2015 Aug. 20; 126(8):1048.
4. Neelapu S S, Tummala S, Kebriaei P, Wierda W, Gutierrez C, Locke F L, Komanduri K V, Lin Y, Jain N, Daver N, Westin J, Gulbis A M, Loghin M E, de Groot J F, Adkins S, Davis S E, Rezvani K, Hwu P, Shpall E J. Nat Rev Clin Oncol. 2018 January; 15(1):47-62. doi: 10.1038/nrclinonc.2017.148. Epub 2017 Sep. 19.
5. Wong C K, Lam C W K, Wu A K L, et al. Plasma inflammatory cytokines and chemokines in severe acute respiratory syndrome. Clin Exp Immunol 2004; 136: 95-103.
6. Mahallawi W H, Khabour O F, Zhang Q, Makhdoum H M, Suliman B A. MERS-CoV infection in humans is associated with a pro-inflammatory Th1 and Th17 cytokine profile. Cytokine 2018; 104: 8-13.
7. Harrison, C. and A. M. Vannucchi, Ruxolitinib: a potent and selective Janus kinase 1 and 2 inhibitor in patients with myelofibrosis. An update for clinicians. Ther Adv Hematol, 2012. 3(6): p. 341-54.
8. Barosi, G., et al., Primary myelofibrosis: Older age and high JAK2V617F allele burden are associated with elevated plasma high-sensitivity C-reactive protein levels and a phenotype of progressive disease. Leuk Res, 2017. 60: p. 18-23.
9. Tefferi, A., et al., Circulating interleukin (IL)-8, IL-2R, IL-12, and IL-15 levels are independently prognostic in primary myelofibrosis: a comprehensive cytokine profiling study. J Clin Oncol, 2011. 29(10): p. 1356-63.
10. Greenfield G, McPherson S, Mills K and McMullin M F. The ruxolitinib effect: understanding how molecular pathogenesis and epigenetic dysregulation impact therapeutic efficacy in myeloproliferative neoplasms. J Transl Med, 2018. 16(1): p. 360.
11. Hechinger, A. K., et al., Therapeutic activity of multiple common gamma-chain cytokine inhibition in acute and chronic GVHD. Blood, 2015. 125(3): p. 570-80.
12. Das, R., et al., Janus kinase inhibition lessens inflammation and ameliorates disease in murine models of hemophagocytic lymphohistiocytosis. Blood, 2016. 127 (13): p. 1666-75.
13. Albeituni, S., et al., Mechanisms of action of ruxolitinib in murine models of hemophagocytic lymphohistiocytosis. Blood, 2019. 134(2): p. 147-159.
14. Sin, J. H. and M. L. Zangardi, Ruxolitinib for secondary hemophagocytic lymphohistiocytosis: First case report. Hematol Oncol Stem Cell Ther, 2017.
15. Wang, J., et al., Ruxolitinib for refractory/relapsed hemophagocytic lymphohistiocytosis. Haematologica, 2019.

Example 3. Mice Bone Marrow Derived Macrophage Isolation and Differentiation

While certain compounds are disclosed, further compounds, such as derivative compounds to those disclosed herein, may be identified using an in vitro bone marrow monocyte derived macrophage (BMDM) activation as described herein.

Notes: Sterile procedure; Reagents: BMM medium: DMEM+10% heat inactivated FBS+1% PS+1% Glu+1000*2-ME+100*NEAA+100*Sodium pyruvate+20 ng/ml M-CSF Day 1: 8-12 week mice, flush bone marrow*4 into 3 ml HBSS in a 50 ml tube, Filter with 70 um cell strainer, Spin down, no need RBC lysis, Re-suspend with 40 ml BMM medium without M-CSF, place cells in two 10 cm dishes (20 ml/dish), Incubate at 37° C., 5% CO2 for 4 hours. This step removes adherent mesenchymal cells or mature macrophages from hematopoietic progenitors.

Day 1, 4 h later: Count two dishes with Cell Counter, Spin down, re-suspend with BMM medium with M-CSF, $1*10^6$/ml, 3 ml/well in 6-well plates 37 C, 5% CO2

Day 4: Collect medium, spin down non-adherent cells, Re-suspend with fresh equal volume BMM medium with M-CSF, return them to the flask, Day 7: Discarding non-adherent cells. Macrophage progenitors adhere to the cell dish and are not washed away. Macrophages are fully differentiated at day 6. Grow cells to be used for phagocytosis assays for 7 d. Add BMM medium with M-CSF plus warm PBS, Il-10 (20, 2000 ng/ml), Il 18 (20, 2000 ng/ml) or combo (2000+2000), Ifng (20 ng/ml), IL4 (20 ng/ml) for 3 more days. The highest concentration (100 ng/mL) of IL-18 used in Applicant's experiments is clinically relevant. Plasma concentrations of IL-18 in excess of 100 ng/mL can be achieved in cancer patients after administration of recombinant human IL-18 in doses that are associated with acceptable toxicity and significant biological activity. For testing drug(s) or drugs combination, drug(s) may be added at day 8 for 2 more days. Collect the naïve cells in RLT buffer Day 10: Collect cells in RLT. Measure macrophage polarization with FACS. Check phagocytosis function with PB or BM cells All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method comprising administering ruxolitinib to an individual having Severe Acute Respiratory Syndrome Coronavirus 2 (SARS-CoV-2) infection-related cytokine storm.

2. The method of claim 1, wherein said individual has SARS-CoV-2 infection-related pneumonia.

3. The method of claim 1, wherein said individual is diagnosed with severe or critical SARS-CoV-2 infection, wherein severe is defined by meeting one or more of respiratory distress, oxygen saturation of less than or equal to 93%, and partial pressure of oxygen in arterial blood (PaO$_2$)/fraction of inspired oxygen (FiO$_2$)≤300 mmHg; and
wherein critical is defined by meeting one or more of respiratory failure needing mechanical ventilation, shock, and other organ failures needing ICU monitoring and treatment.

4. The method of claim 1, wherein said individual is diagnosed with SARS-CoV-2 infection confirmed by PCR.

5. The method of claim 1, wherein said individual is aged between greater than or equal to 18 years.

6. The method of claim 1, wherein said individual is diagnosed with a B cell deficiency, and wherein said individual is further administered a second therapeutic agent selected from an antiviral antibody, an anti-serum, an antiviral therapy, or combinations thereof.

7. The method of claim 1, wherein said individual has one or more of cardiovascular disease (CVD), rheumatoid arthritis (RA), hepatitis, and diabetes.

8. The method of claim 1, wherein said ruxolitinib is administered to an individual at a dose of about 5 mg/day, about 10 mg/day, or about 15 mg/day, or about 20 mg/day, or about 25 mg/day, or about 30 mg/day, or about 35 mg/day, or about 40 mg/day, or about 45 mg/day, or about 50 mg/day, or about 55 mg/day, or about 60 mg/day, or about 65 mg/day, or about 70 mg/day, or about 75 mg/day, or about 80 mg/day, or about 85 mg/day, or about 90 mg/day, or from about 10 to about 100 mg/day, or about 25 to about 75 mg per day, or about 30 to 50 mg/day, or from about 100 to about 200 mg/day, or greater than 200 mg/day.

9. The method of claim 1, wherein said administration is carried out once a day, twice a day, three times a day, more than four times a day, or continuously administered throughout a day.

10. The method of claim 1, wherein said administration is carried out until complete clinical remission.

11. The method of claim 1 wherein said administration is oral administration.

12. The method of claim 1, further comprising administering a therapeutic agent selected from baricitinib, tofacitinib, INREBIC (Fedratinib), a TYK2 inhibitor, metformin, rapamycin, a corticosteroid, an anti-viral, and combinations thereof.

13. The method claim 1, wherein said administration is carried out in the absence of a steroid.

14. The method of claim 1, comprising administering one or both of rapamycin and metformin to said individual, before, during, or after administration of ruxolitinib.

15. A method comprising administering a dose of at least 5 mg ruxolitinib to an individual having Severe Acute Respiratory Syndrome Coronavirus 2 (SARS-CoV-2) infection-related cytokine storm, wherein said administration is oral; and
wherein said dose is administered at least twice a day.

16. A method comprising orally administering a dose of ruxolitinib to an individual having Severe Acute Respiratory Syndrome Coronavirus 2 (SARS-CoV-2) infection-related cytokine storm, and wherein said dose is selected from about 5 mg, about 10 mg, and about 15 mg.

17. The method of claim 16, wherein said dose is 5 mg.

18. The method of claim 16, wherein said dose is 10 mg.

19. The method of claim 16, wherein said dose is 15 mg.

20. The method of claim 16, wherein said dose is administered at least twice a day.

21. A method comprising administering ruxolitinib to an individual having Severe Acute Respiratory Syndrome Coronavirus 2 (SARS-CoV-2) infection-related cytokine storm, said individual having one or more of:
a respiratory rate of greater than 30 breaths/minute;
oxygen saturation of less than or equal to 93% in a resting state; and
a partial pressure of oxygen in arterial blood/fraction of inspired oxygen less than or equal to 300 mm Hg.

22. The method of claim 21 wherein said ruxolitinib is administered in a 5 mg dose.

23. The method of claim 21, wherein said dose is 10 mg.

24. The method of claim 21, wherein said dose is 15 mg.

25. The method of claim 21, wherein said dose is administered at least twice a day.

26. The method of claim 21, wherein said administration is oral.

* * * * *